US00RE37829E

(19) United States
(12) Reissued Patent
Charhut et al.

(10) Patent Number: US RE37,829 E
(45) Date of Reissued Patent: Sep. 3, 2002

(54) AUTOMATED PRESCRIPTION VIAL FILLING SYSTEM

(75) Inventors: Kenneth A. Charhut, Tokyo (JP); Keith Goodale, Park City, IL (US); Joseph Blechl, Ingleside, IL (US); Will Skou, Des Plaines, IL (US)

(73) Assignee: AutoMed Technologies, Inc., Vernon Hills, IL (US)

(21) Appl. No.: 09/232,743

(22) Filed: Jan. 15, 1999

Related U.S. Patent Documents

Reissue of:
(64) Patent No.: 5,208,762
Issued: May 4, 1993
Appl. No.: 07/622,991
Filed: Dec. 6, 1990

U.S. Applications:

(63) Continuation of application No. 08/434,693, filed on May 4, 1995, now abandoned.

(51) Int. Cl.[7] ..... G06F 7/00
(52) U.S. Cl. ..... 700/216; 221/9; 53/493; 700/224
(58) Field of Search ..... 700/213–244; 221/2–9, 12, 15, 174; 53/493, 154, 411, 64; 414/807

(56) References Cited

U.S. PATENT DOCUMENTS

| | | | | | |
|---|---|---|---|---|---|
| 2,665,775 | A | * | 1/1954 | Smith | 186/1 |
| 2,708,996 | A | * | 5/1955 | Skillman | 194/10 |
| 2,865,532 | A | * | 12/1958 | Smith | 221/13 |
| 3,023,851 | A | * | 3/1962 | Stiller | 186/1 |
| 3,144,958 | A | * | 8/1964 | Gumpertz | 221/7 |
| 3,160,793 | A | * | 12/1964 | Colburn et al. | 221/7 |
| 3,179,288 | A | * | 4/1965 | Davy | 221/15 |
| 3,185,851 | A | * | 5/1965 | D'Emilio | 250/223 |
| 3,196,276 | A | * | 7/1965 | Naab | 250/223 |
| 3,206,062 | A | * | 9/1965 | Rappaport | 221/7 |
| 3,310,199 | A | * | 3/1967 | Roberts et al. | 221/25 |
| 3,312,372 | A | * | 4/1967 | Cooper, Jr. | 222/2 |
| 3,410,450 | A | * | 11/1968 | Fortenberry | 221/7 |
| 3,417,542 | A | * | 12/1968 | Merrill et al. | 221/93 |
| 3,436,736 | A | * | 4/1969 | Platt et al. | 364/DIG. 2 |
| 3,556,342 | A | * | 1/1971 | Guarr | 221/2 |
| 3,599,152 | A | * | 8/1971 | Williams | 221/71 |
| 3,653,176 | A | * | 4/1972 | Gess | 53/64 |

(List continued on next page.)

FOREIGN PATENT DOCUMENTS

| | | |
|---|---|---|
| CA | 936501 | * 11/1973 |
| GB | 1168758 | * 10/1969 |
| GB | 1411951 | * 10/1973 |
| JP | 51-792 | 1/1976 |
| JP | 52-047400 | * 12/1977 |
| JP | 61-104904 | 5/1986 |
| JP | 63-208410 | 8/1988 |
| JP | 64-28102 | 1/1989 |
| JP | 1-288265 | 11/1989 |
| JP | 2-28417 | 1/1990 |

OTHER PUBLICATIONS

"Future Distribution System—Picking, AutoSorting, Reading" published by Nikkan Kogho Shimbun, Ltd., Mar. 1979, pp. 197–203 and 214–218.

*Primary Examiner*—William Grant
*Assistant Examiner*—Steven R. Garland
(74) *Attorney, Agent, or Firm*—Jansson, Shupe & Munger, Ltd.

(57) ABSTRACT

A method and apparatus for dispensing drugs, wherein a patient's order of one or more prescriptions is automatically filled. Various drugs are stored in three or more filler lines. A vial size is assigned to each line. When a prescription is filled, it is automatically assigned to a line in view of the vial size requirements and processed accordingly. Provisions are made for the inability to fill a prescription or order. Subsequently, all of the patient's prescriptions are collected and made available as a single order.

34 Claims, 20 Drawing Sheets

U.S. PATENT DOCUMENTS 3,730,388 A * 5/1973 Bender ..... 221/68
3,732,544 A * 5/1973 Obland ..... 364/479
3,780,907 A * 12/1973 Colburn et al. ..... 221/2
3,815,780 A * 6/1974 Bauer ..... 221/15
3,837,139 A * 9/1974 Roseburg ..... 221/7 X
3,885,702 A * 5/1975 Joslin et al. ..... 221/174
3,917,045 A * 11/1975 Williams et al. ..... 221/71 X
4,267,942 A * 5/1981 Wick, Jr. et al. ..... 221/2
4,434,602 A * 3/1984 Culpepper ..... 53/473
4,546,901 A * 10/1985 Buttarazzi ..... 221/10
4,573,606 A * 3/1986 Lewis et al. ..... 221/2
4,655,026 A * 4/1987 Wigoda ..... 364/479 X
4,664,289 A * 5/1987 Shimizu et al. ..... 221/2
4,674,259 A * 6/1987 Hills ..... 53/202
4,674,651 A * 6/1987 Scidmore et al. ..... 221/3
4,693,057 A * 9/1987 Rittinger et al. ..... 53/539
4,695,954 A * 9/1987 Rose et al. ..... 364/479 X
4,766,542 A * 8/1988 Pilarczyk ..... 364/401 X
4,767,023 A * 8/1988 Hackmann et al. ..... 221/152
4,805,377 A 2/1989 Carter ..... 53/415
4,869,392 A * 9/1989 Moulding, Jr. et al. ..... 221/1
4,918,604 A * 4/1990 Baum ..... 364/413.01
4,971,513 A * 11/1990 Bergerioux et al. ..... 414/807
4,980,292 A * 12/1990 Elbert et al. ..... 435/289
4,984,709 A * 1/1991 Weinstein ..... 221/7
5,018,644 A * 5/1991 Hackmann et al. ..... 221/65
5,047,948 A * 9/1991 Turner ..... 364/479

* cited by examiner

MAIL ORDER/ PICK UP SCANNER MESSAGE ?
NO
YES
BIN ASSIGNED ?
NO
YES
BIN FOR THIS CONVEYOR ?
NO
YES
SEND MESSAGE TO MAIL ORDER/PICK UP EXTRACTION FOR THIS BIN

ENTRY IN STAGING OUTPUT QUEUE ?
NO
YES
TIME DELAY BASED ON GATE#
OPEN GATE FOR THIS RX
DELAY FOR RX DROP
CLOSE GATE
FREE UP ACCUMULATOR AREA

AUTOMATED PRESCRIPTION VIAL FILLING SYSTEM

Matter enclosed in heavy brackets [ ] appears in the original patent but forms no part of this reissue specification; matter printed in italics indicates the additions made by reissue.

*RELATED APPLICATION*

*This application is a continuation of U.S. patent application Ser. No. 08/434,693 filed May 4, 1995, now abandoned, which is a reissue patent application of U.S. Pat. No. 5,208,762 (Charhut et al.) issued May 4, 1993.*

BACKGROUND OF THE INVENTION

The present invention generally relates to methods and apparatus for dispensing prescriptions. More specifically, the invention relates to methods and apparatus for dispensing and filling containers, such as vials, with medications.

Generally, out-patients have been provided with prescriptions in one of two ways. One way is to provide oral, solid prescriptions that are pre-filled in vials at a remote location and kept in inventory at a pharmacy. These pre-filled vials are removed from stock when needed and relabelled with patient specific information. Another method involves filling prescriptions by having a pharmacist hand-count the required drugs from a bulk supply and then place a patient specific label on a vial.

There are disadvantages to both of these prescription filling methods. If pharmacists elect to use pre-filled vials, they must carry an inventory of several hundred drug types. Further, they must manage inventory levels and monitor stock for expiring products. Generally, a pharmacist will pay a premium for having the vials pre-filled.

On the other hand, filling prescriptions from bulk on an individual basis is very labor intensive and subject to human accounting errors. Further, servicing a large out-patient population requires large numbers of pharmacists.

Many out-patient facilities use a combination of these two systems, supplying pre-filled vials on high volume products and hand-filling vials with products that are less in demand.

SUMMARY OF THE INVENTION

The present invention provides an improved method and apparatus for dispensing prescriptions. The invention eliminates the need for pre-filled vials and greatly reduces the number of pharmacists required to service a large out-patient population. To these ends, the invention provides an automated prescription vial filling system.

In an embodiment, the invention provides a system whereby a pharmacist inputs a patient's order including prescription and patient identification information via a computer terminal. The system processes the information and automatically fills one or more vials with one or more drugs, and then automatically labels and caps the vials containing drugs, pursuant to the -pharmacist's order. When all of the patient's prescriptions are filled, the order is accumulated by an intelligent conveyor and presented to the pharmacist as the patient's complete order, ready for pick-up or mailing.

In an embodiment, the invention provides that a system for accomplishing the foregoing consists of at least one line of machines that will automatically fill, label, cap, and sort vials with one or more prescriptions in accordance with a patient order. Each line fills a vial of a certain size with medication. The three lines preferably are identical with the exception of the vial size used. Vial sizes are determined by prescription quantity, drug mix, and drug volume of the institution where the system is placed. A typical size distribution could be 60 cc, 120 cc, and 250 cc vial sizes.

Located at an end of the three lines is a sorting conveyor. The conveyor places the patient's complete order together for pickup or mailing.

An advantage of the invention is the ability to employ a minimum number of technicians or pharmacists for counting drugs to be dispensed. Another advantage of the invention is the reduction and inventory of pre-filled drug vials.

Another advantage of the invention is a prescription filling system that provides cost reductions such as for labor and purchases of bulk medication over current filling methods.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
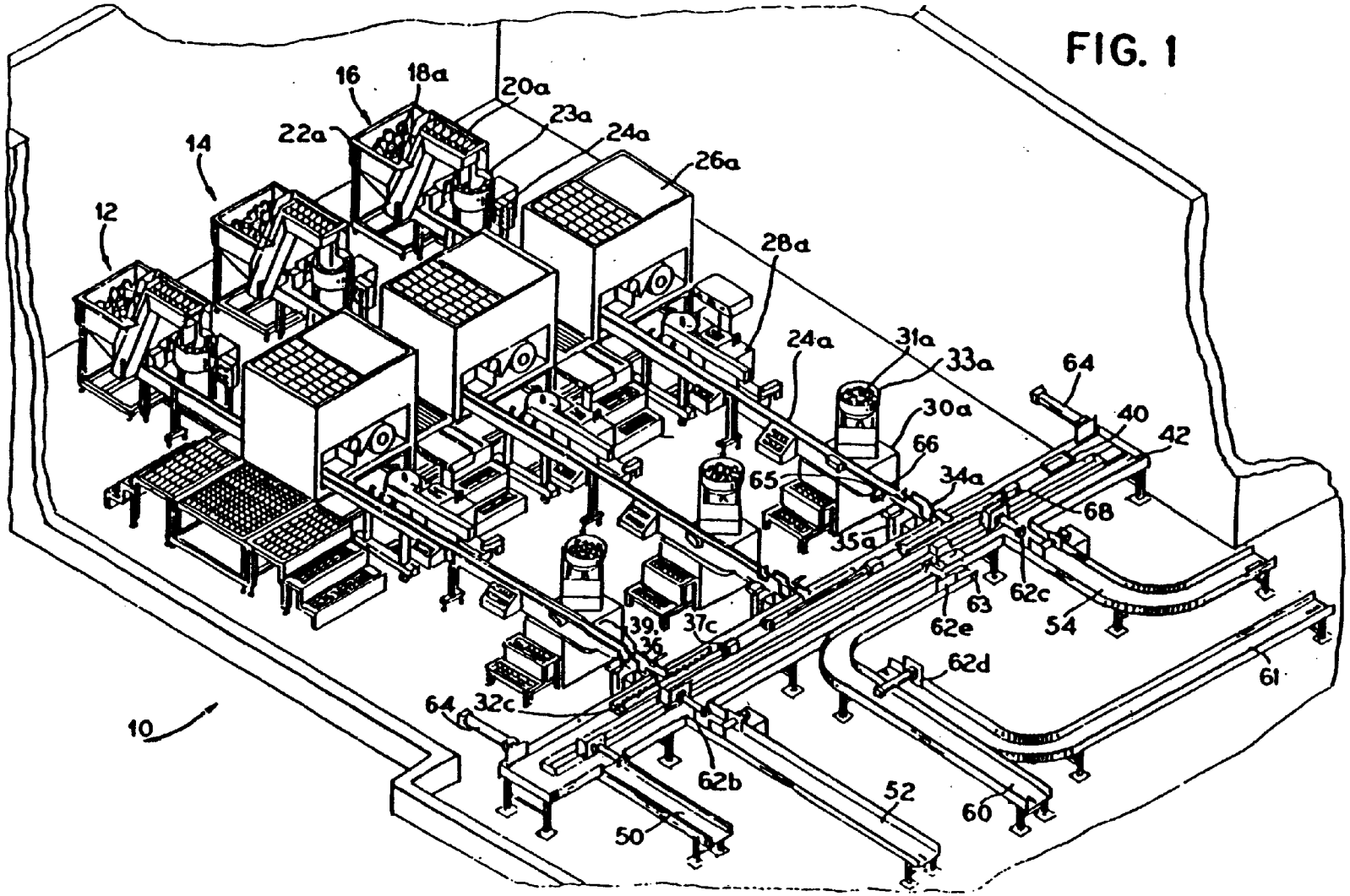
FIG. 1 is a perspective view of an embodiment of the system of the present invention.
Figure 2:
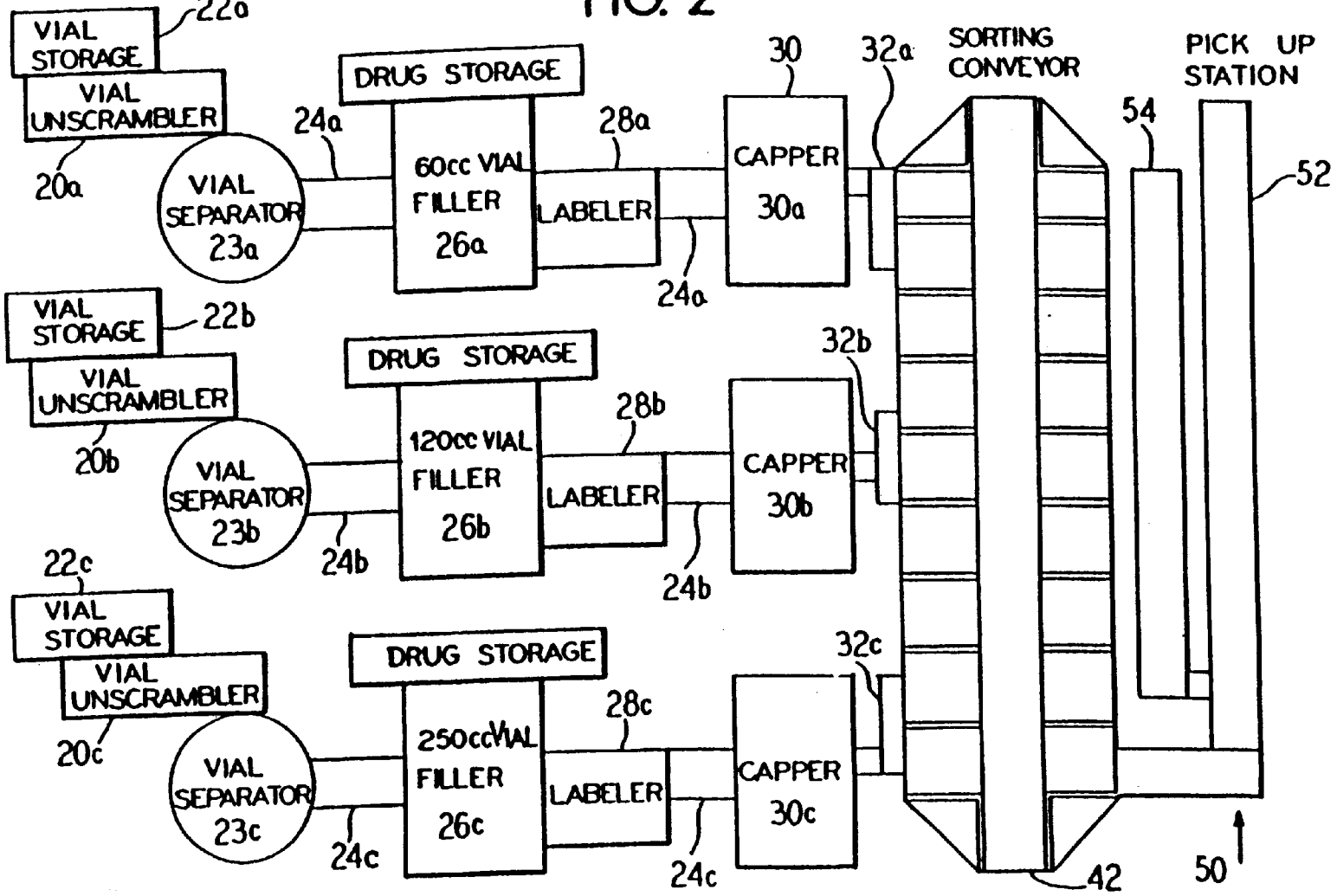
FIG. 2 is a schematic for the system of FIG. 1.
Figure 3:
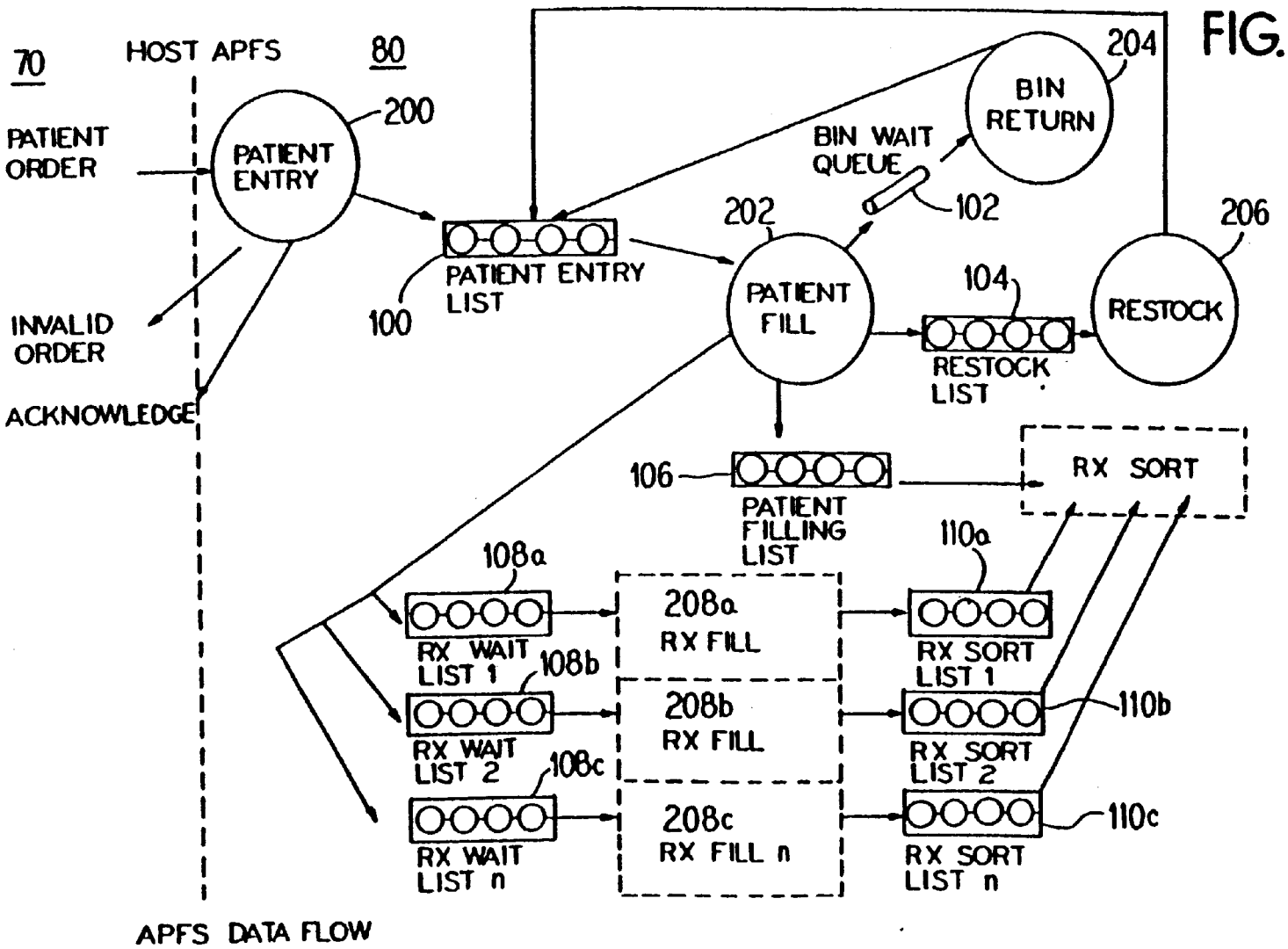
FIG. 3 is a data flow diagram for the system of FIG. 1.
Figure 4:
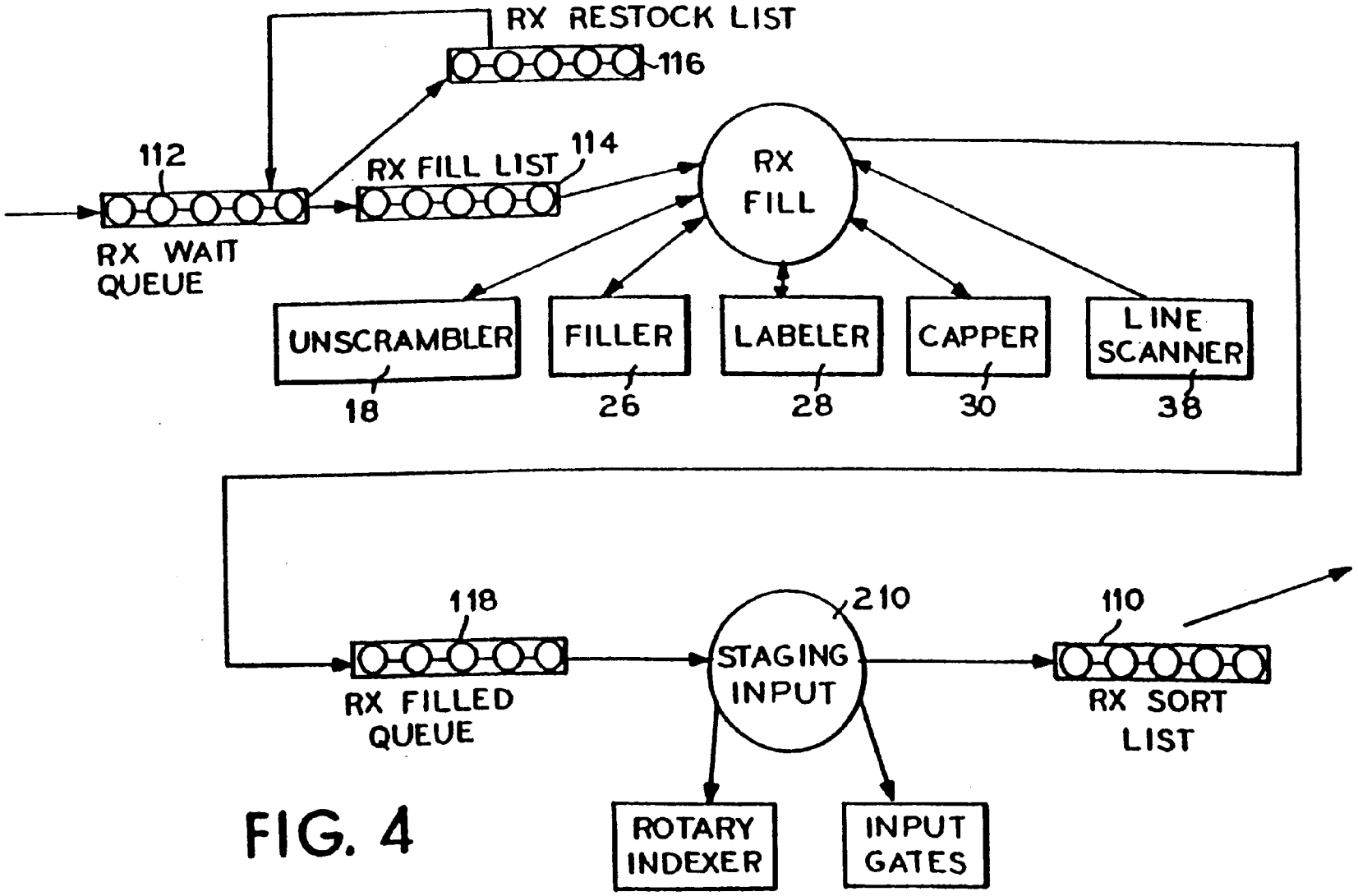
FIG. 4 is a prescription fill flow diagram for the system of FIG. 1.
Figure 5:
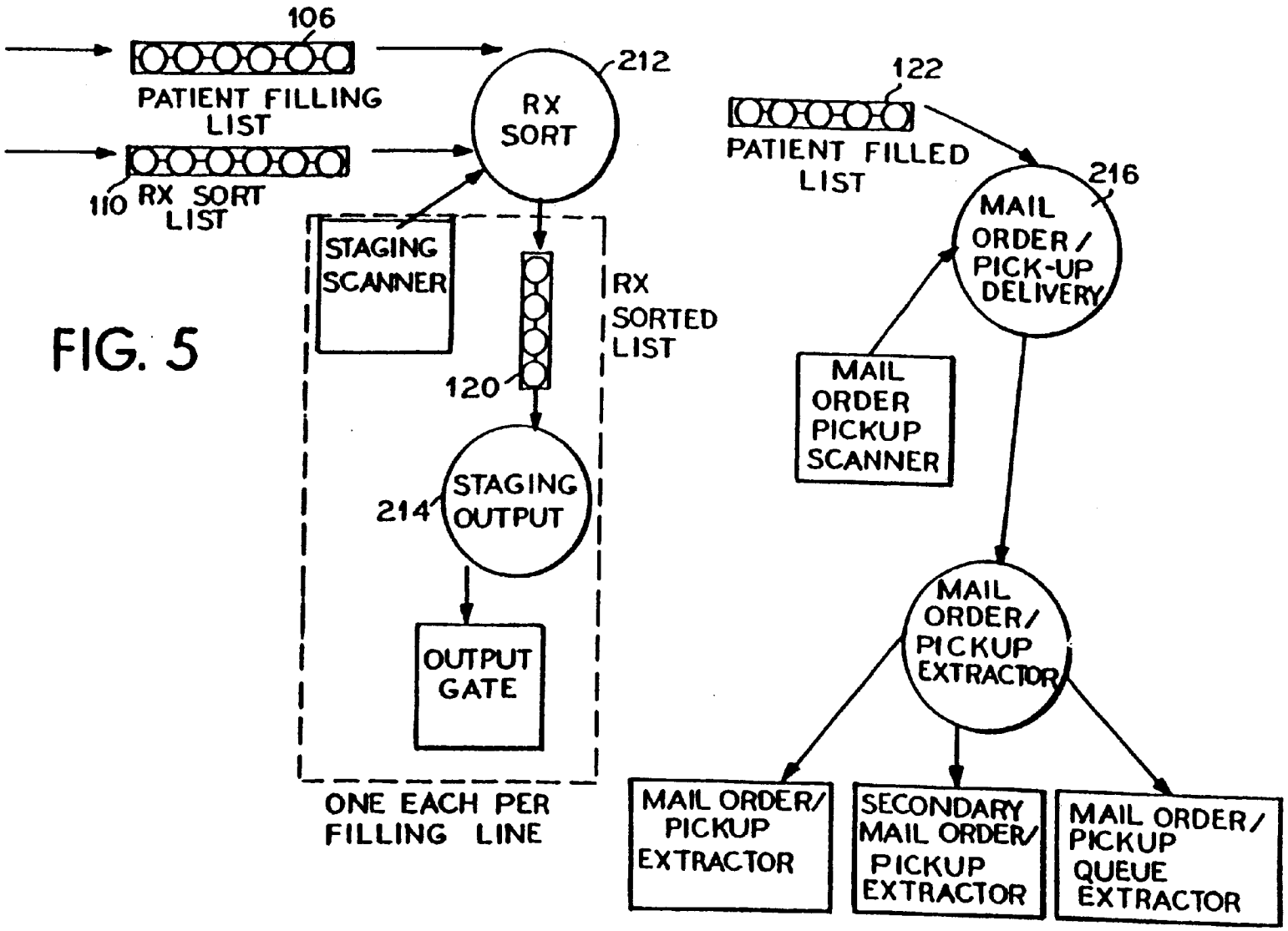
FIG. 5 is a prescription sort data flow diagram for the system of FIG. 1.

In accordance with the invention, a system is provided for dispensing prescriptions, preferably for out-patients, wherein the system packages an order of one or more prescriptions in view of patient prescription information and then presents a complete patient's order to a pharmacist for pick-up or delivery. Such a system is illustrated in FIGS. 1 and 2. Data flow diagrams for such a system are illustrated in FIGS. 3–5. Processes employed in the system are described below.

As illustrated in FIGS. 1 and 2, a system 10 is provided which includes three lines 12, 14 and 16 of machines that can automatically fill, label, cap, and sort vials 18 in accordance with a patient's prescription order under the control of an appropriate control system. While three lines are depicted in the illustrated embodiment, the present invention encompasses any number of lines. Preferably, the lines are identical with the exception of the vial sizes filled. While vial sizes will be determined by prescription quantity, drug mix, and drug volume of an institution in which the system 10 is used, a typical vial size distribution could be 60 cc, 120 cc, and 250 cc.

For ease of understanding, only one of lines 12, 14, and 16 will be described in detail. However, it should be apparent that, with the exception of vial size, the description is applicable to each of lines 12, 14, and 16. Therefore, reference numerals identifying items in the drawings which have counterparts associated with each line will be used generically in this description, but in the drawings will carry additional designations such as a, b, and c to identify those items corresponding to the particular lines.

The first machine position at each line of the system is a vial unscrambler 20. In such a machine, vials of one size are dumped into a hopper 22 in bulk form. The hopper 22 preferably is large enough to hold approximately about 1100 vials, about a days supply.

The unscrambler 20 orients the vials upright in a separator 23 and spaces them on a conveyor 24 ready to feed into a vial filler 26. The unscrambler 20 can also be equipped to shoot a blast of air into the vial, cleaning debris that might be present. Preferably, the unscrambler 20 comprises a machine similar to an Omega Model number 20-LP manufactured by Omega Design Corporation, 211 Philips Road, Lionville, Pa. or a New England Machinery Model NEHE-50J or NEHB-50AJ manufactured by New England Machinery, Inc., 6204 29th Street East, Bradenton, Fla.

From the unscrambler 20, a vial will travel via the conveyor 24 to the vial filler 26 (also referred to as the filler). The vial filler 26 preferably comprises a modified Automatic Tablet Control machine manufactured by Sanyo Corporation in Japan and distributed by Baxter Health Care Corporation, One Baxter Parkway, Deerfield, Ill. under the mark ATC. This ATC machine or automatic tablet control, is capable of holding up to about 480 different oral, solid medications. Such medications are held in canisters calibrated specifically for those drugs. There can be one or more ATC machines per line depending on drug mix and drug volume required by the institution in which the system 10 is installed.

The conveyor 24 brings the vial under a filling position of the filler 26 and a signal from the controller system activates the appropriate drug canister, as required. More than one canister can be assigned to a specific drug and can dispense doses simultaneously. The drug doses are counted into the vial until filling is complete.

After filling, the vial is labeled by a label machine 28 (also referred to as the labeler), which an preferably be similar to Avery Model ALX 910 available from Avery Label Division, 35 McLachlan Drive, Rexdale, Ontario, Canada or a Willett Model 2600 manufactured by Willette America, Inc., 4901 Northeast Parkway, Fort Worth, Texas. The labeler 28 can be located downstream of the vial filler 26 as shown or it can preferably be located under the vial filler 26 to label vials during or immediately following filling. A signal from the control system is sent to the label machine 28 at the same time the vial is being filled. The label machine print human readable information, as well as bar code information on demand. The label information is kept in a data base and contains drug description, as well as any warning statements.

After the label is printed, a reader can be provided associated with the labeler 28, to verify the contents of the label by reading the printed bar code.

Once a vial is filled and labelled, it travels down the conveyor 24 to a capping machine 30 (also referred to as the capper). The capping machine 30 grasps the vial and preferably applies a child-resistant cap 31 to the vial.

As illustrated, just after the capper 30, each line includes a bar code reader 36 and a wrap belt 39 disposed on opposite sides of the conveyor 24. The wrap belt 39 serves to spin a vial around so that the bar code thereon can be read by the reader 36. The bar code reader 36 verifies the legibility of the bar code on the label and confirms the prescription number to the control system.

After the vial is capped, a sensor associated therewith verifies that the cap has been properly applied. The capper 30 preferably includes a reservoir 33 that is sufficiently large to store one full shift's supply of caps. The preferred capping machine can be one similar to Kalish-Cap Mark III manufactured by HG Kalish Inc., 6535 Mill Creek #62, Mississauga, Ontario, Canada or Capamatic DLR-1 manufactured by National Instrument Co., 4119 Fordleight Road, Baltimore, Md.

Once a vial has been capped and the contents are verified by the capper sensor 36, it proceeds to an accumulator or accumulation station 32 positioned at the end of its respective conveyor 24 (accumulator 32c is illustrated most clearly in FIG. 1). The accumulation station 32 serves two functions: sorting and ejecting Vials are ejected when they have an improper drug count, unreadable labels, or improperly seated caps. A signal sent by the filler 26, labeller 28, or capper 30 causes a defective vial to be ejected into a reject bin 35 by a blast of pneumatic air gun 34 if any of the situations is detected. When a vial is ejected, the control system places a refill request with the filler 26 on a priority basis so that another attempt is made to complete the prescription order.

A circulating conveyor 42 (also referred to as a sorting conveyor) carries circulating bins 40 along a path that brings each of the bins under an accumulator 32 once per rotation. The bins 40 are bar coded and the control system assigns at least one circulating bin 40 per patient. If a particular patient has more vials than a single bin can hold, a second or third bin will also be assigned. A bin 40 will circulate the conveyor 42 until a patient's total order has been collected. The bar code on the bin 40 will be read by bar code reader 63 prior to travel under the accumulators 32 and a signal will correctly time an accumulator 32 to discharge a specific patient's vial into the bin 40.

All properly bottled vials are assigned to a location on the accumulator 32 where they await a circulating bin 40 in which they are to be placed. These locations are also referred to as the staging output area. The accumulator 32 preferably has up to twenty locations for temporary vial storage.

The accumulators 32 are positioned above the conveyor 42 so that the vials awaiting on an accumulator can be placed into a passing bin 40. To this end, each accumulator 32 has associated therewith a pneumatic gripper 37 on a rodless cylinder for placing upon command, a vial into an accumulator position.

One or more of the bins is assigned to a patient by the control system. As the assigned circulating bin(s) 40 move (s) under the vial accumulator 32, the accumulator 32 drops the vials into the assigned bin(s). The drop of the vials is effectuated by means of a released door contained in the accumulator position on which the vials rest and which is activated by a solenoid controlled by the control system. Preferably, the accumulator 32 is capable of placing its entire contents in one bin, if necessary. In this manner, all of the vials for one patient's order can be sorted and placed together in a bin.

When a patient's total order has been accumulated in one or more bin(s) 40, the sorting conveyor 42 transfers the bin(s) 40 to one of a plurality of spurs.

Spur 50 is a conveyor referred to as the exception conveyor. An order is placed on spur 50 if, for some reason, the contents must be modified due to error.

The spur 50 can also be used to place medications other than oral solids into a patient's bin 40. This spur 50 can carry a bin 40 under a rack that contains, for example, liquids or creams. By reading the bar code on the bin 40, the rack automatically would discharge the correct medication into the bin 40.

Spur 52 is a conveyor referred to as the mail order conveyor. An order is placed on spur 52 if it is to be mailed to a patient.

Spur 54 is a conveyor referred to as the pick-up conveyor. An order is placed on spur 54 if it is to be picked up by a patient, e.g. a walk-in.

As illustrated, a variety of extractors are operatively positioned to move bins onto and off of the conveyors 42, 50, 52, 60, and 61. These extractions are generally designated by the numeral 62. Extractor 62a, upon command, diverts bins from conveyor 42 into conveyor 50. Extractor 62b, upon command, diverts bins from conveyor 42 onto conveyor 52. Extractor 62c, upon command, diverts bins from conveyor 42 onto conveyor 54. Extractor 62d, upon command, diverts returned bins from conveyor 61 onto conveyor 60. Extractor 62e, upon command, diverts returned bins from conveyor 60 onto conveyor 42.

Additionally, a scanner 63 is provided that reads bar codes on returned bins.

An empty bin 40 is placed on a return conveyor 60 or 61 which places it back on the circulating conveyor 42. A return conveyor 60 is used to return bins used for mail orders, while return conveyor 61 is used to return bins used for pick-up orders. At the point of return, the bar code on the bin (40) will be read and noted in the control system as an available bin. If the bar code is unreadable, the bin 40 is automatically ejected from the system 10.

The return is located just downstream from the take-off on the circulating bin conveyor 42 so the circulating conveyor 42 will always be full.

Overhead transfer cylinders 64 are used to transfer bins 40 from one straight conveyor 42a to another straight conveyor 42b, which together form the circulating conveyor 42.

In FIGS. 3–5, the data flow for various aspects of the system is illustrated. As illustrated in FIG. 3, a host computer 70 provides a patient's order information to a control system 80. In return, the control system 80 advises the host computer 70 as to whether an order is valid or invalid.

In the data flow diagram, several items such as data units, smart boxes, registers, etc. are identified. These are discussed first.

The Patient Entry List 100 is a collection of patient orders received by the control system 80 from the host computer 70. Generally, the orders are organized in a first-in, first-out (FIFO) manner. However, when orders receive priority status, e.g. during a refill as described above, a latter order can be placed at the head of the list so that it will be processed first.

Each entry on the Patient Entry List includes patient specific information, for identification purposes, and one or more prescriptions for a patient.

The Bin Wait Queue 102 is used to temporarily hold a patient's order pending availability of one of the circulating bins 40. This is a FIFO queue and when a bin 40 becomes available, the order held the longest is assigned to that bin 40.

The Restock List 104 is a FIFO list which is used whenever a drug canister does not contain a sufficient quantity to fill a patient's order. When such is the case, the unfilled order is removed from the Patient Entry List and placed at the end of the Restock List until the designated canister is filled.

The Patient Filling List 106 is a FIFO list used once it has been determined that an order can be filled by the system 10. Once such a determination is made, a patient's order is transferred from the Patient Entry List and placed at the end of the Patient Filling List.

The Prescription Wait Lists 108 are FIFO lists that has been determined that a patient's order can be filled. For every filling list 12, 14 and 16 in the System 10, there is a dedicated Prescription Wait List. When such a determination is made, a prescription in a patient's order is placed at the tail end of the appropriate Prescription Wait List Prescriptions are removed from a Prescription Wait List in the order received.

The Prescription Sort Lists 110 are randomly accessible lists used once prescriptions have been filled One Prescription Sort List 110 is provided for each of the lines 12, 14, and 16. Once a prescription is filled, the prescription is placed at the end of its respective Prescription Sort List 110. At that time, the associated vial will be sitting in the accumulator 32.

The Prescription Sort Lists are used by the control system 80, as discussed below, to place vials in the staging area into the correct bin 40. Prescriptions are randomly removed from these lists as they are placed into their bins.

Figure 6:
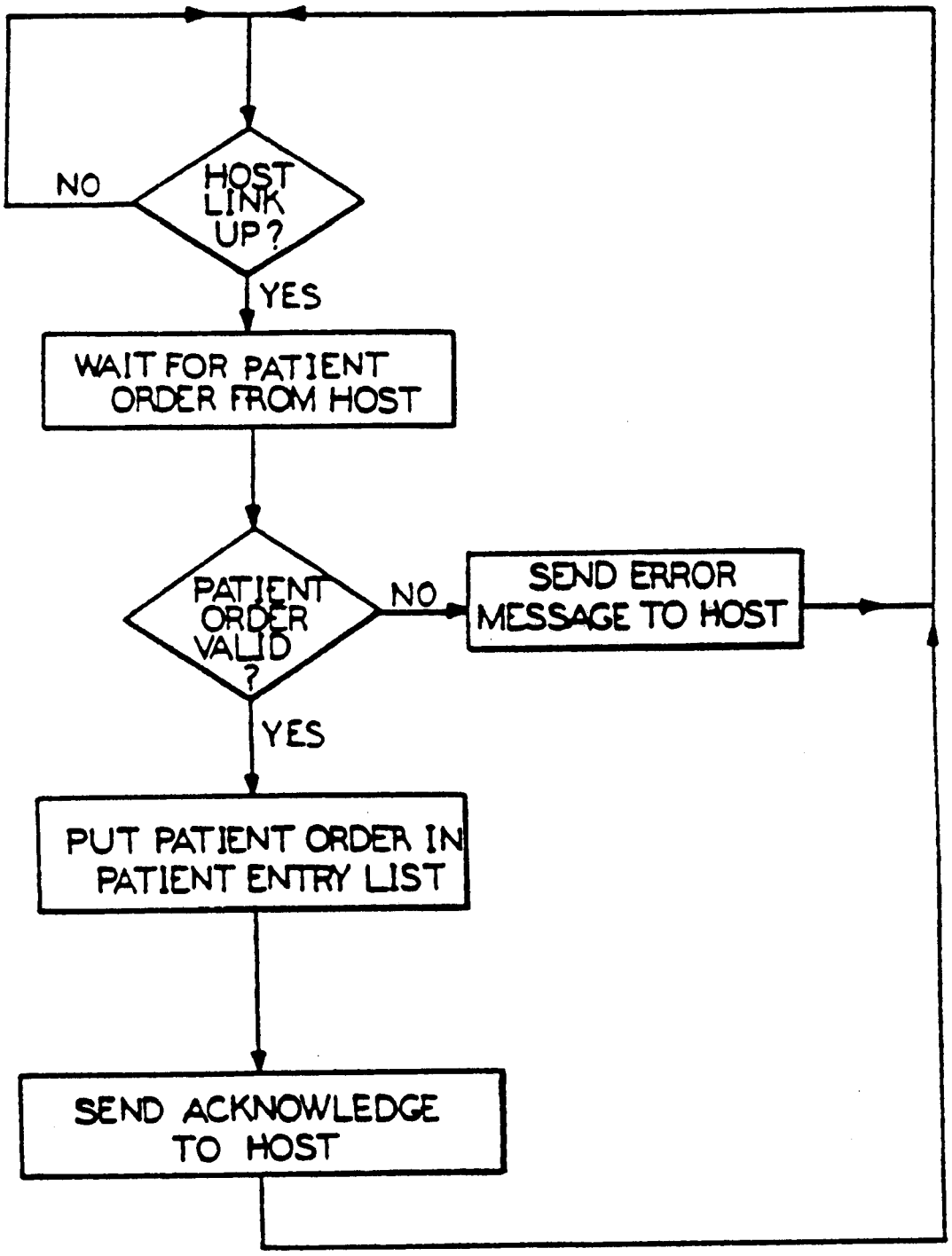
FIG. 6 is a flow diagram for a patient entry process.

As illustrated in FIG. 6, the Prescription Wait Queue 112 are generally FIFO lists containing listings of prescriptions to be filled by the filler 26. One Prescription Wait Queue is provided for each filler 26. When a prescription is assigned to a line for filling, it is transferred from its associated Prescription Wait List 108 to this list.

The Prescription Fill Lists 114 are used when vials are to be filled. One Prescription Fill List 114 is produced for each filler 26. When an accumulator area becomes available, as discussed below, prescriptions are taken off of the associated Prescription Wait Queue and placed at the tail end of the Prescription Fill List. At that time, a vial is positioned on the filling line for the prescription. After a prescription is filled and left waiting to enter the accumulator 32, it is removed from this list.

The Prescription Restock Lists 116 are FIFO lists used whenever a prescription cannot be filled by the associated filler 26. One Prescription Restock List 116 is provided for each filler 26.

If it is determined, as discussed below, that a filler 26 cannot fill a prescription, the prescription is transferred from its associated Prescription Wait Queue 112 to this list until the filler 26 is restocked. Then, the prescription is reinserted in a Prescription Wait Queue 112 at the head of the list.

The Prescription Filled Queues 118 are used after vials have passed their line scanners. One Prescription Filled Queue is provided for each filling line. When such is the case, a prescription is placed at the tail end of the Prescription Filled Queues. Each entry in a Prescription Filled Queue 118 is flagged to indicate the specific accumulator area to which the associated vial is to be sent or if the vial is to be directed to the reject bin. Since vials pass through the rotary indexes in a FIFO manner, this is a FIFO queue.

As illustrated in FIG. 5, the Prescription Sorted List 120 is used when a vial is about to be dropped into its assigned bin 40. Prescriptions are transferred to this list from the Prescription Sort Lists 110, as described below, when a determination is made to drop a vial into a bin 40. Prescriptions are deleted from this list after staging output processing.

The Patient Filled List 122 is used after a patient's order has been filled. When such is the case, a patient's order is removed from the Patient Filling List 106 and placed at the tail end of the Patient Filled List 122.

The Patient Filled List 122 is used by the mail order/pick-up delivery process to deliver a bin 40 to the correct destination handling area from the sorting conveyor 42. Once a bin has been physically removed from the sorting conveyor 42, the patient's order is removed from the list.

With the foregoing description, of the various lists and queues employed in the control system 80, the various processes employed by the system 10 under the control of the control system 80 will now be described.

PATIENT ENTRY PROCESS

As illustrated in FIG. 6, the patient data entry process 200 can be described as follows: first, it is determined by the control system 80 whether the host computer 70 is linked up thereto. If not, then the control system 80 sits in a "wait" state. If the host is linked up, then the control system 80 waits for a patient's order information to be provided from the host computer 70. Once the patient order is received, the control system 80 determines whether the patient order information is valid. If the information is not valid, then an error message is sent to the host computer to inform the operator of the error. If the patient order information is valid, then the patient's order, comprising one or more prescriptions and patient specific data, is placed on the Patient Entry List as described above and illustrated in FIG. 3. Subsequently, an acknowledgement is sent to the host computer 70 to inform the operator thereof that the patient order was placed on the Patient Entry List.

PATIENT FILL PROCESS

Figure 7:
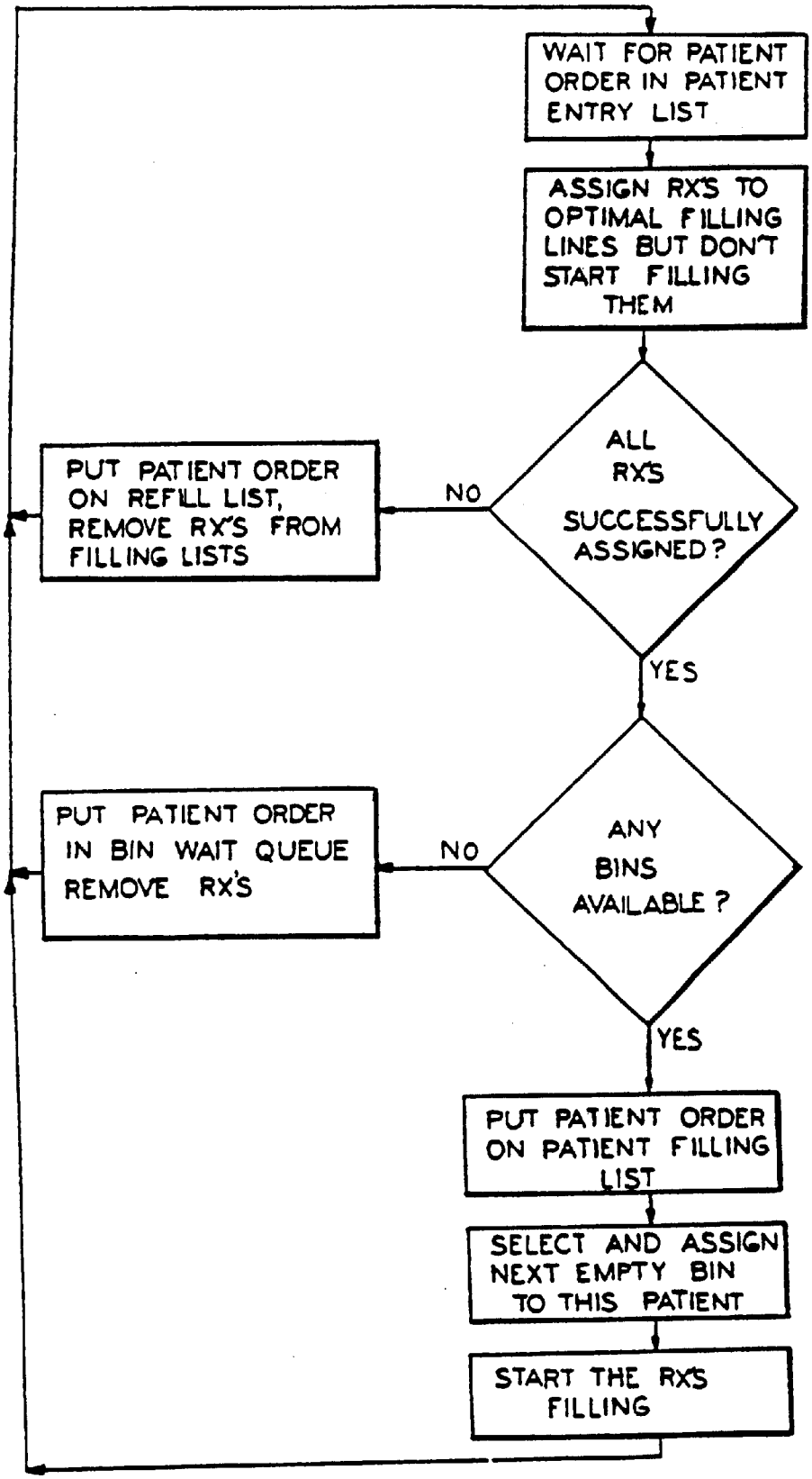
FIG. 7 is a flow diagram for a patient fill process.

The patient fill process is the process by which a patient's order is divided into its various prescriptions which are then assigned to the various lines 12, 14, and 16. As illustrated in FIG. 7, in this process, the system waits for a patient's order to be placed in the Patient Entry List 100. For every patient order in the Patient Entry List 100, a prescription filling assignment is provided to each of the filling lines 12, 14 and 16 so that the fill process is accomplished in an optimal manner. However, the prescriptions are not filled at this time.

Subsequently, it is determined whether the prescriptions are successfully assigned to the various lines. If not, the patient order is placed on the Re-fill List 104 and the prescriptions are removed from the Prescription Filling Lists 114. If the prescriptions are successfully assigned, it is determined whether a bin 40 is available for receipt of the patient order. If a bin is not available, then the patient order is placed in the Bin Wait Queue 120 and the prescriptions are removed from the Prescription Fill Lists 114. The process 202 then again waits for a patient's order information to be presented in the Patient's Entry List.

If a bin 40 is available, then the patient's order is placed on the Patient Filling List 106 and an optimal bin 40 is selected and assigned to this patient, as discussed below. Subsequently, the process for filling prescriptions commences.

ASSIGNMENT OF PRESCRIPTIONS TO OPTIMAL FILLING LINE

Figure 8:
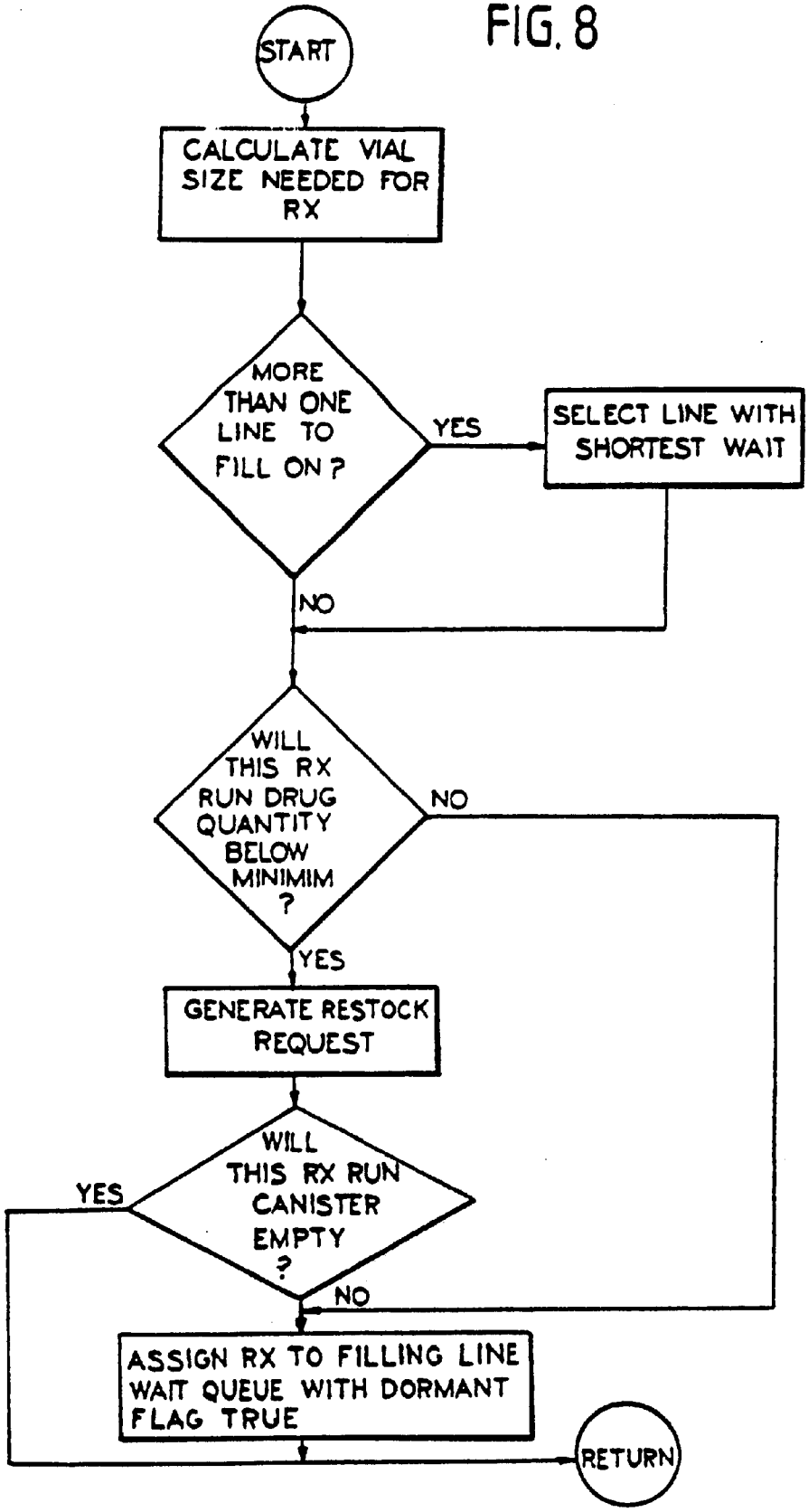
FIG. 8 is a flow diagram for a process for assignment of prescriptions to optimal filling line.

A simple process is used to determine the optimal filling line assignment for a prescription. As illustrated in FIG. 8, first, a vial size is calculated for a particular prescription. Then it is determined if more than one line is available for filling the prescription. If more than one line of the same vial size is available to fill the prescription, then the line with the shortest wait is selected, otherwise, the first available line is selected. Subsequently, it is determined whether the filling of this particular prescription will deplete the drug quantity of the selected line below a minimum. If the answer is yes, then a restock request is generated to indicate to the system operator or pharmacist to restock the canisters. Then it is determined whether the prescription will fully deplete the associated canister. If the answer is yes, then the process is terminated and non-assignment is indicated.

Figure 9:
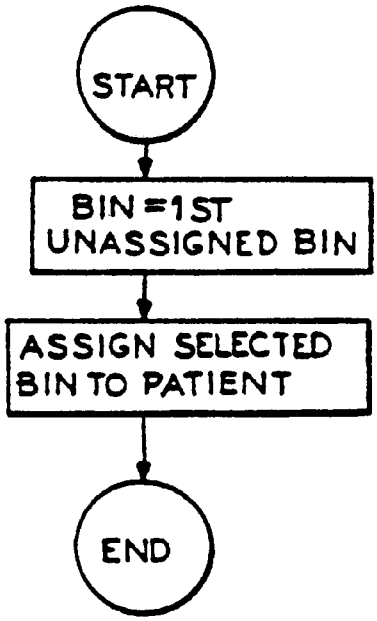
FIG. 9 is a flow diagram for a process for selection and assignment of optimal bins.

If it is determined that the filling of the prescription will not run the drug quantity below a minimum or that filling the prescription will not run a canister empty, then the prescription is assigned to the associated Prescription Wait List 108 with a dormant flag set to true. At start up all bins are empty and resting on the return conveyor. Bins from return conveyor are placed on sorting conveyor by the overhead transfer mechanism 62. Bins travel on sorting conveyor through bar code reader 63 which reads bin number. Software recognizes bin as being the first unassigned bin available (see FIG. 9), as it keeps track of all bin numbers and assigns them to patient orders.

BIN RETURN PROCESS

The Bin Return Process 204 primarily moves bins from the return conveyor 60 back onto the sorting conveyor 42. Secondarily, it determines if any patient's orders are in the Bin Wait Queue 102 and, if so, places such orders at the head of the patient's entry list so that they are processed next.

Figure 10:
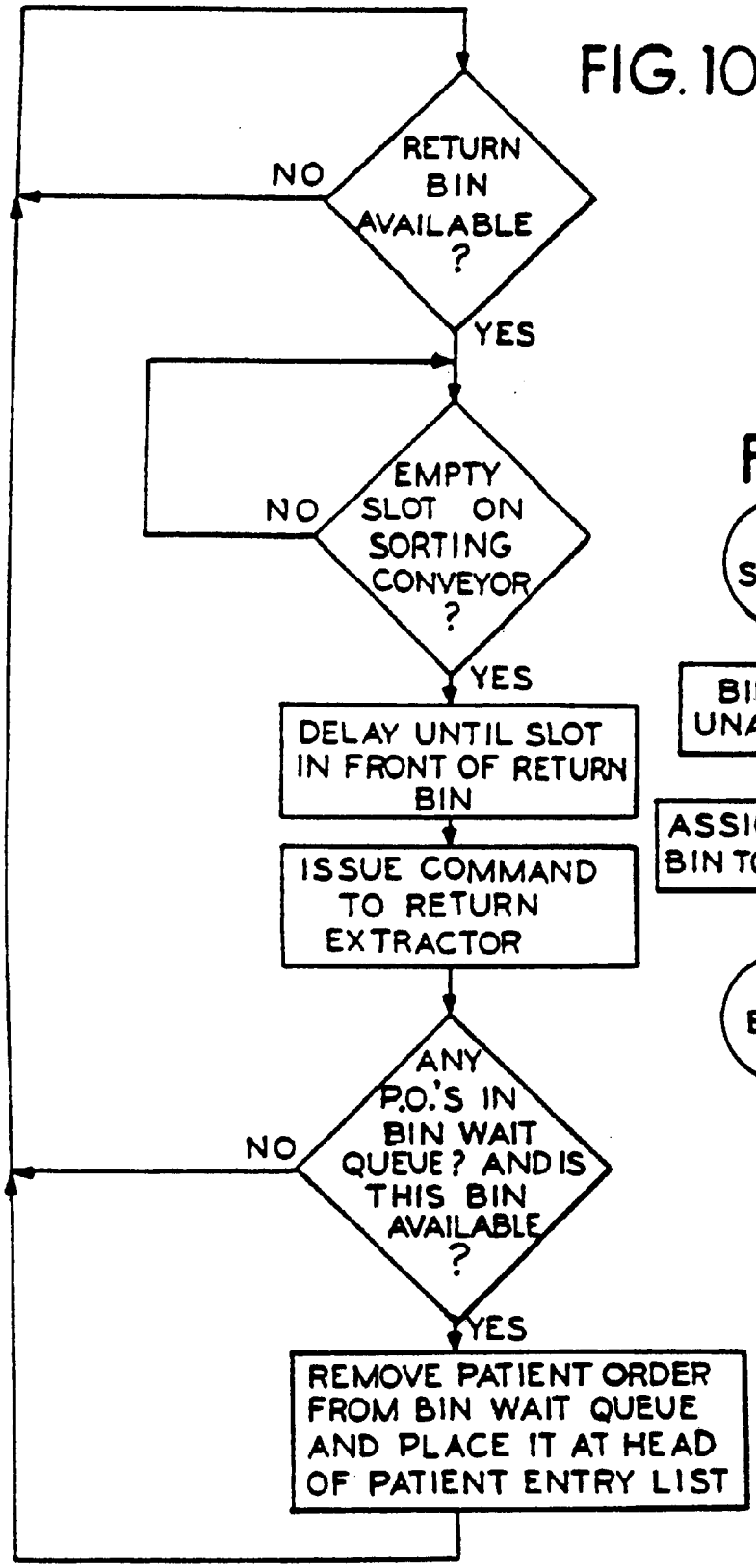
FIG. 10 is a flow diagram for a bin return process.

As illustrated in FIG. 10, at the beginning of this process it is determined whether a return bin is available. If a return bin is available, then a second determination is made as to whether an empty slot on the sorting conveyor is available. If an empty slot is not available, then this process sits in a loop until an empty slot is available.

If an empty slot on the sorting conveyor is available, then a delay is imposed until such slot travels to a position in front of the return bin. Then, a command is issued to the return bin extractor.

After the following issuance of the command to the return bin extractor, a determination is made as to whether any patient orders ar in the Bin Wait Queue and whether the particular bin is available. If the determination is negative, then the entire process is repeated. Otherwise, the patient's order information is removed from the Bin Wait Queue and placed at the head of the Patient Entry List 100. Then the entire process recommences.

RESTOCK PROCESS

Figure 11:
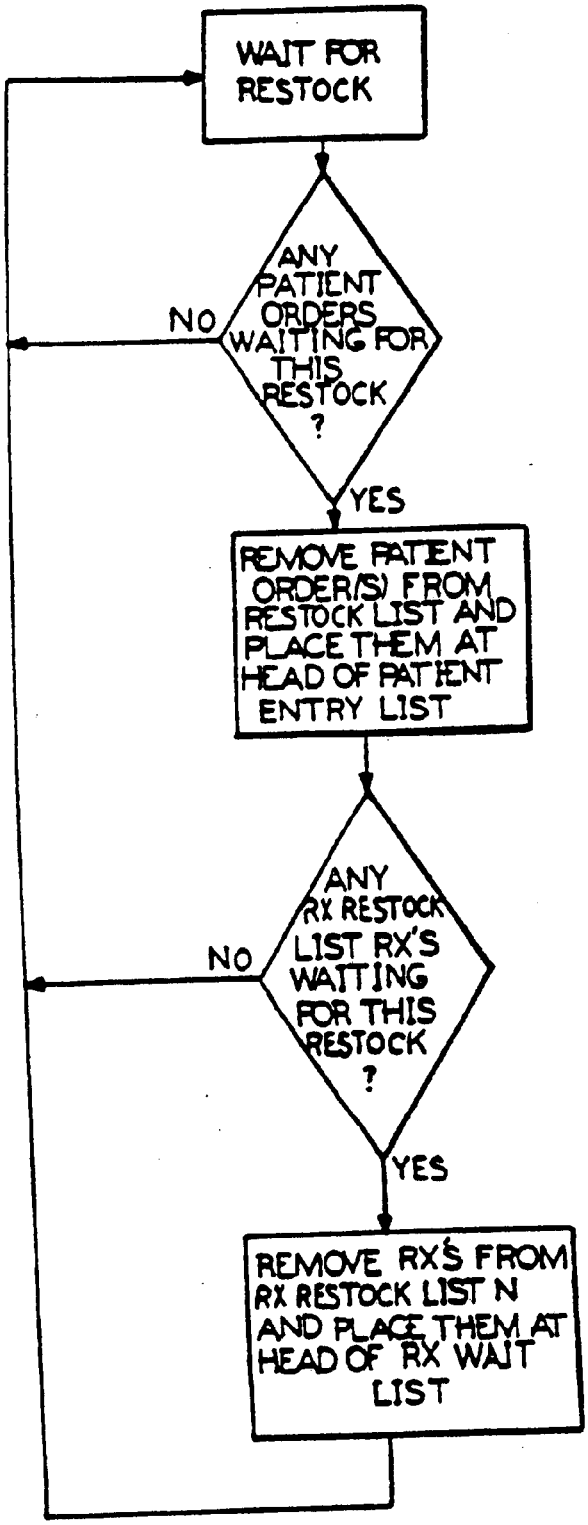
FIG. 11 is a flow diagram for a re-fill process.

The Restock Process 206 is invoked if any drug canister should not have a quantity sufficient to fill any prescription within a patient's order. As illustrated in FIG. 11, the Patient Fill Process 202 takes the order off the Patient Entry List 100, as described above and transfers it to the Restock List 104 until the drug canister required has been restocked.

In the Restock Process 206, a continuous routine waits in a loop for indicators that a drug canister has been restocked. Then a determination is made as to whether any patient orders in the restock List are waiting for the indicated restock. If no orders are waiting for the indicated restock, the routine recommences. Any patient order placed in the Restock List waiting for this restock is removed and placed at the head of the Patient Entry List 100. Otherwise, it is determined whether any prescriptions on a Prescription Restock List 116 are waiting for the indicated restock. If the answer is negative, then the restock routine returns to the beginning. If the answer is affirmative, the prescriptions are removed from the Restock List 116 and placed at the associated head of the Prescription Wait Queue 112. Then, the restock routine returns to the beginning to wait for a further indication of a restock.

PRESCRIPTION FILL PROCESS

A Prescription Fill Process 208 is actually a collection of processes, lists, and hardware interfaces as illustrated in FIG. 4. For every filling line in the system, there is a Prescription Fill Process 208.

Figure 12:
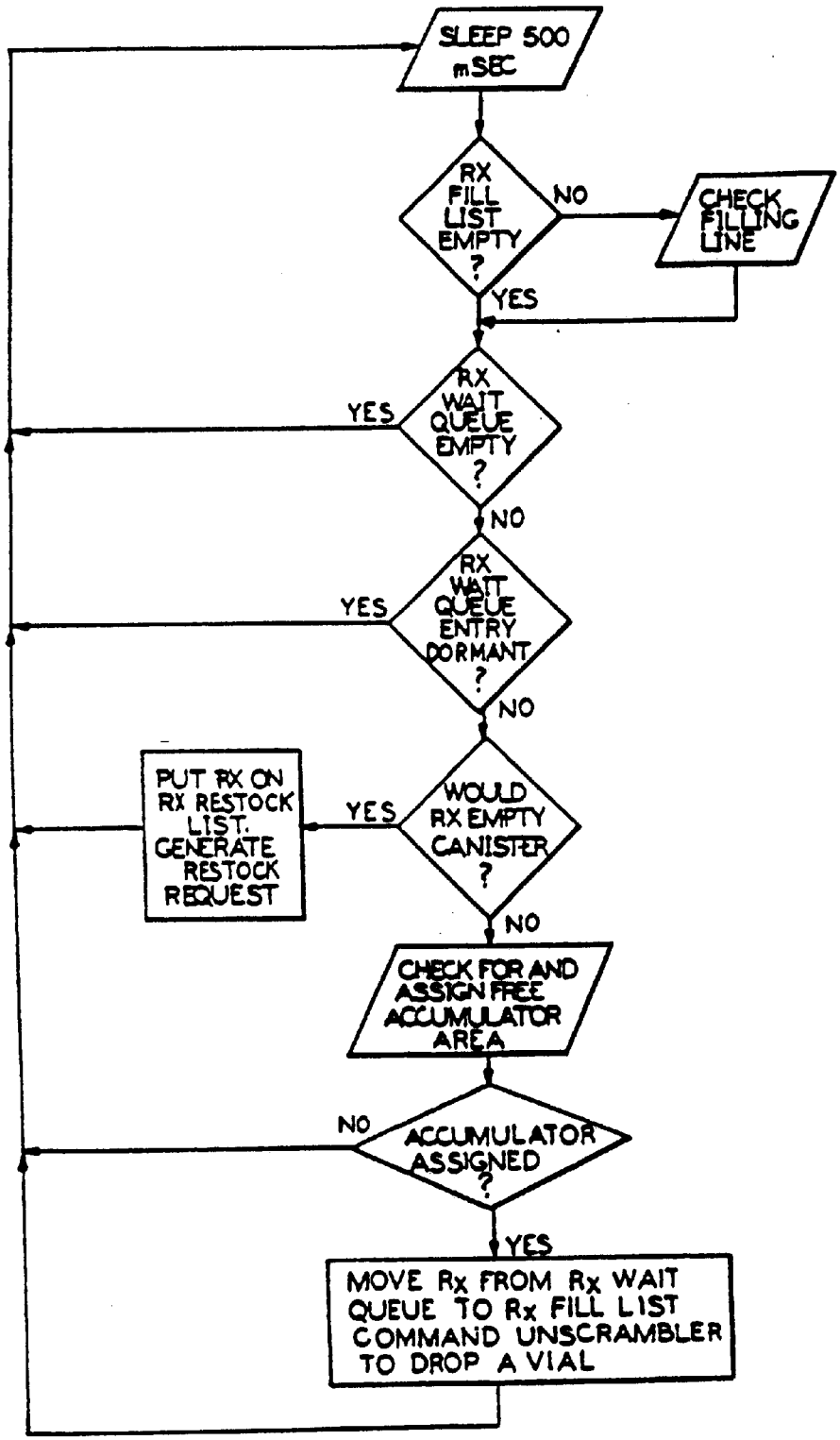
FIG. 12 is a flow diagram for a prescription fill process.

As illustrated in FIG. 12, in this process 208, a routine commences with a wait or sleep state of about 500 ms. Then a determination is made as to whether an associated Prescription Fill List 114 is empty. If the Prescription Fill List 114 is not empty, then a check is made of the associated filling line, as described below.

After the associated filling line is checked, or if the associated Prescription Fill List 114 is empty, then a determination is made as to whether the associated Prescription Wait Queue 112 is empty. If the Prescription Wait Queue 112 is empty, then the routine returns to the beginning. Otherwise, a determination is made as to whether the Prescription Wait Queue 112 entry dormant flag is set to true. If the Prescription Wait Queue 112 entry dormant flag is set to true, then the routine recommences. Otherwise, a determination is made as to whether the filling of the prescription would empty the requisite drug canister. If the filling of the prescription would empty the requisite drug canister, then the prescription is placed on the associated Prescription Restock List 116 and a restock request is generated. Then the routine recommences.

If filling of the prescription would not empty the requisite drug canister, then a check for an assignment of a free accumulator area is made.

If the accumulator 32 does not include free area for assignment, then the routine is recommenced. Otherwise, if a free area of the accumulator 32 is assignable, then the prescription is removed from the Prescription Wait Queue 112 and moved to the associated Prescription Fill List 114. At the same time, a command is issued to the associated unscrambler 18 to drop a vial.

CHECK FILLING LINE FUNCTION

Figure 13:
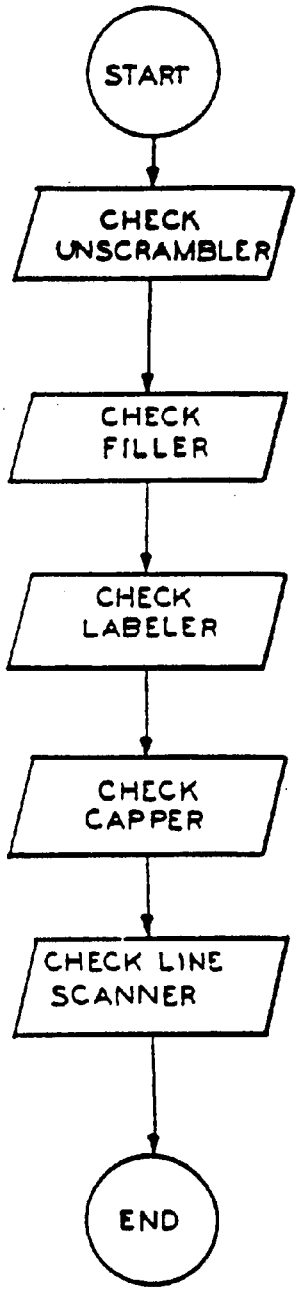
FIG. 13 is a flow diagram for a check filling line function.

As illustrated in FIG. 13, the check of a filling line made during a Prescription Fill Process 208 commences with a check of the associated unscrambler 18 and continues with a check of the associated filler 26, labeller 28, capper 30, and line scanner 38.

UNSCRAMBLER CHECK

Figure 14:
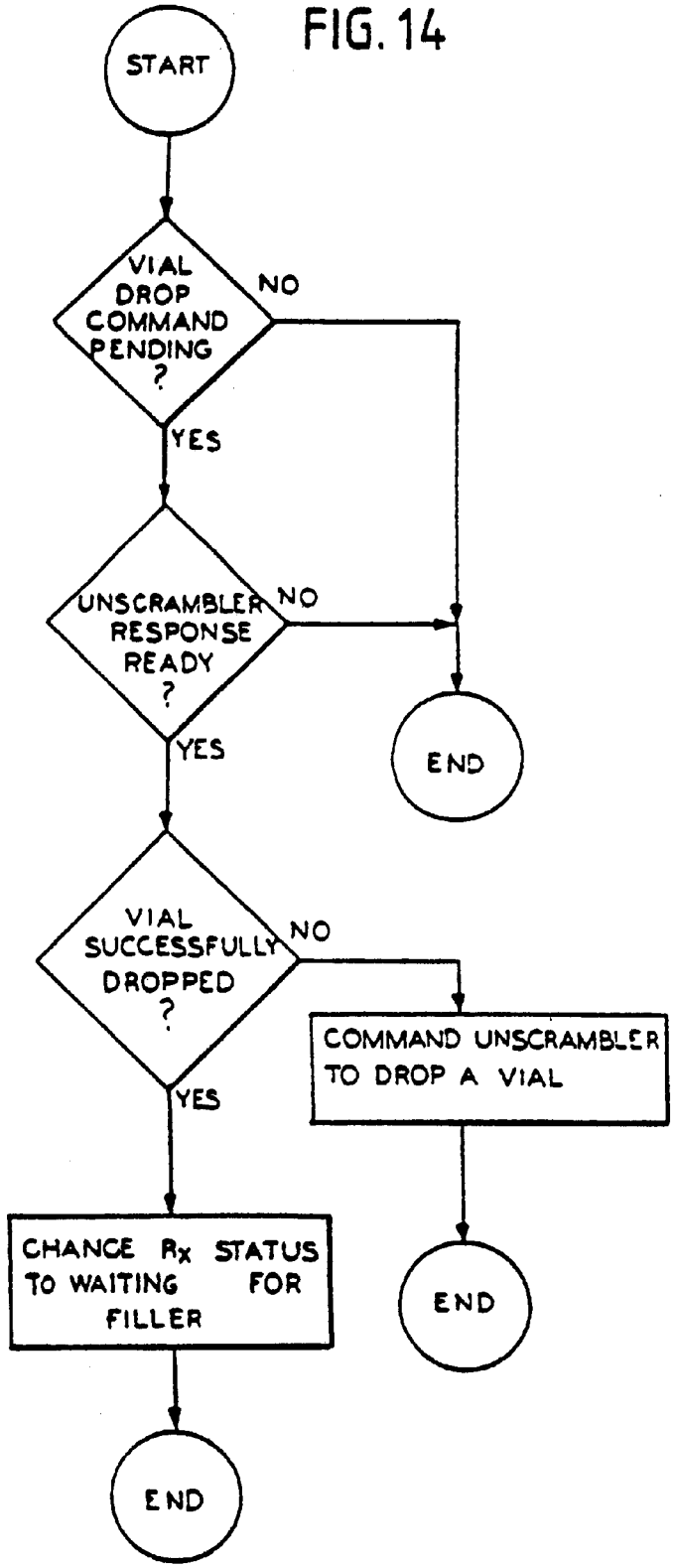
FIG. 14 is a flow diagram for an unscrambler check process.

As illustrated in FIG. 14, when the unscrambler is checked, a determination is made as to whether a vial drop command is pending. If no vial drop command is pending, then the check is discontinued. If a vial drop command is pending, then a determination is made as to whether the unscrambler is ready to respond. If the unscrambler is not ready to respond, then the check is terminated. If the unscrambler is ready to respond, then a determination is made as to whether a vial has been successfully dropped. If a vial has not been successfully dropped, then a command is issued to the unscrambler to drop a vial and the scrambler check is terminated.

FILLER CHECK

Figure 15:
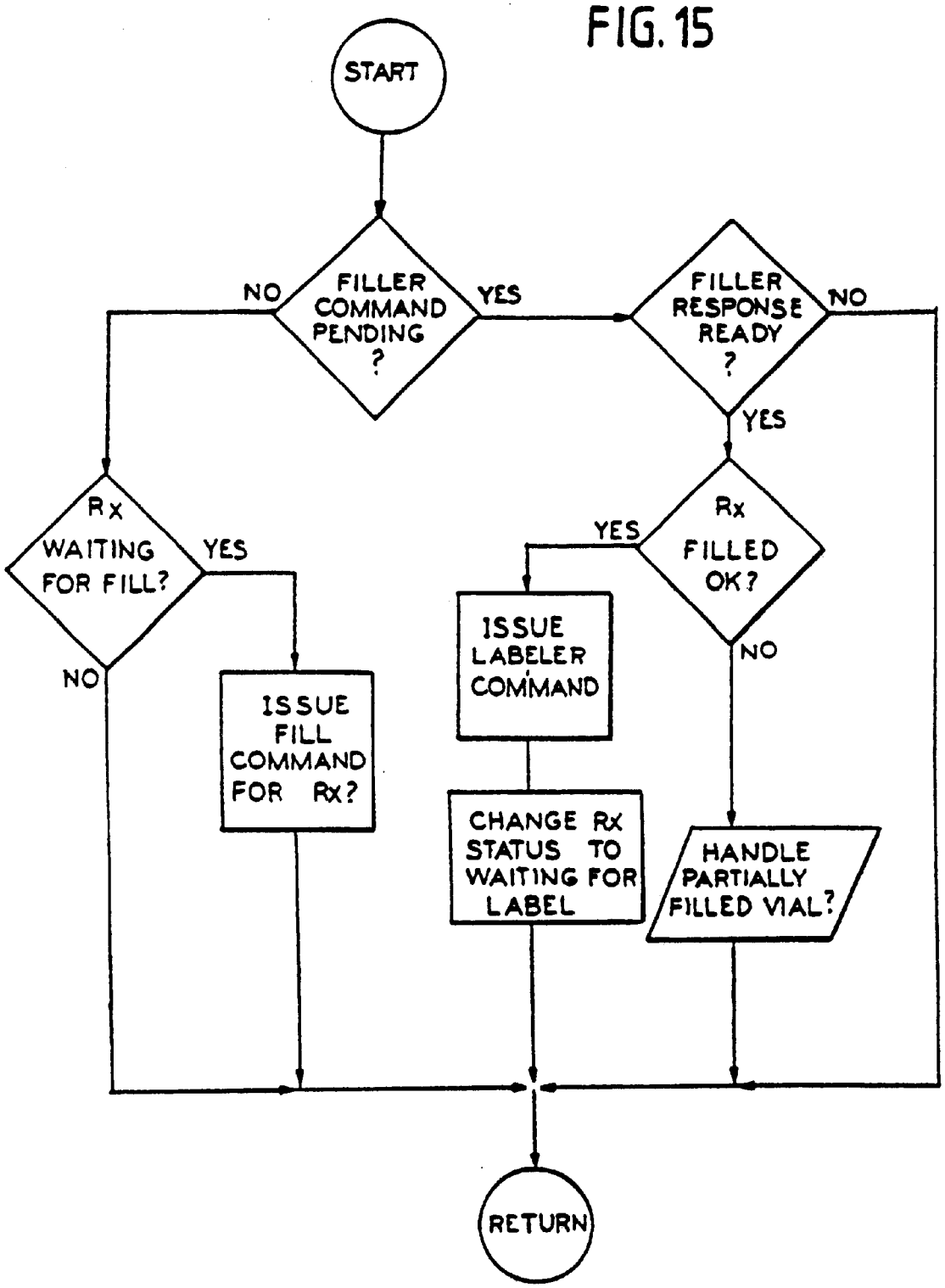
FIG. 15 is a flow diagram for a filler check process.

As illustrated in FIG. 15, if a vial has been successfully dropped, then the prescription is assigned a status of "waiting for filler" and a check is then made of the filler 26.

The check of the filler commences with a determination which is made as to whether a filler command is pending. If a filler command is not pending, then a determination is made as to whether a prescription is assigned the status "waiting for filling." If no prescription is assigned the status "waiting for filling," then the check of the filler is terminated. If a prescription is assigned the status "waiting for filling," then a command is issued to the filler to fill the prescription. Then the check of the filler is terminated.

If at the beginning of the check of the filler, it is determined that a filler command is pending, then a determination is made as to whether a filler response is ready. If a filler response is not ready, then the check of the filler is terminated. If a filler response is ready, then a determination is made as to whether a prescription has been successfully filled. If a prescription has not been successfully filled, then a signal is issued to alert the system of the partially filled vial and the vial is handled appropriately. Then the check of the filler is terminated.

If it is determined that a prescription has been successfully filled, then a command is issued to the labeller to apply a label to the vial. Then the prescription is assigned a status of "waiting for label" and the check of the filler is terminated.

LABELER CHECK

Figure 16:
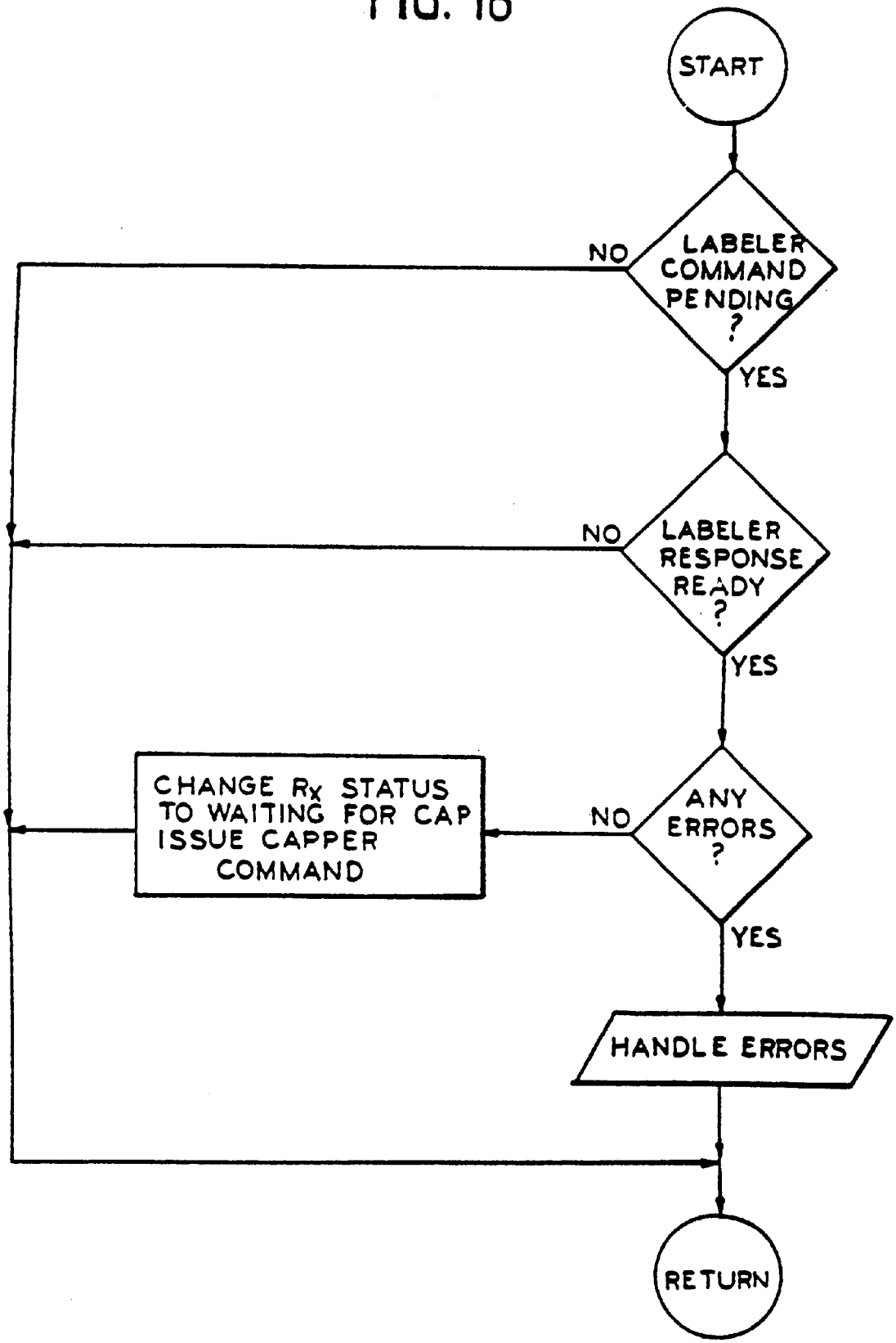
FIG. 16 is a flow diagram for a labeler check process.

As illustrated in FIG. 16, when the labeller is checked, a routine is executed that, as a first step, determines whether a labeller command is pending. If no labeller command is pending, then the routine is terminated. If a labeller command is pending, then a determination is made as to whether a labeller response is ready. If no labeller response is ready, then the routine is terminated. If a labeller response is ready, then a determination is made as to whether any errors have occurred in the filling process. If no errors have occurred, then the prescription is assigned a status of "waiting for capping" and a command is issued to the capper to cap the vial. Then the routine is terminated.

If an error in the filling process is detected, then an error handling routine is invoked and the labeller checking routine is terminated.

CAPPER CHECK

Figure 17:
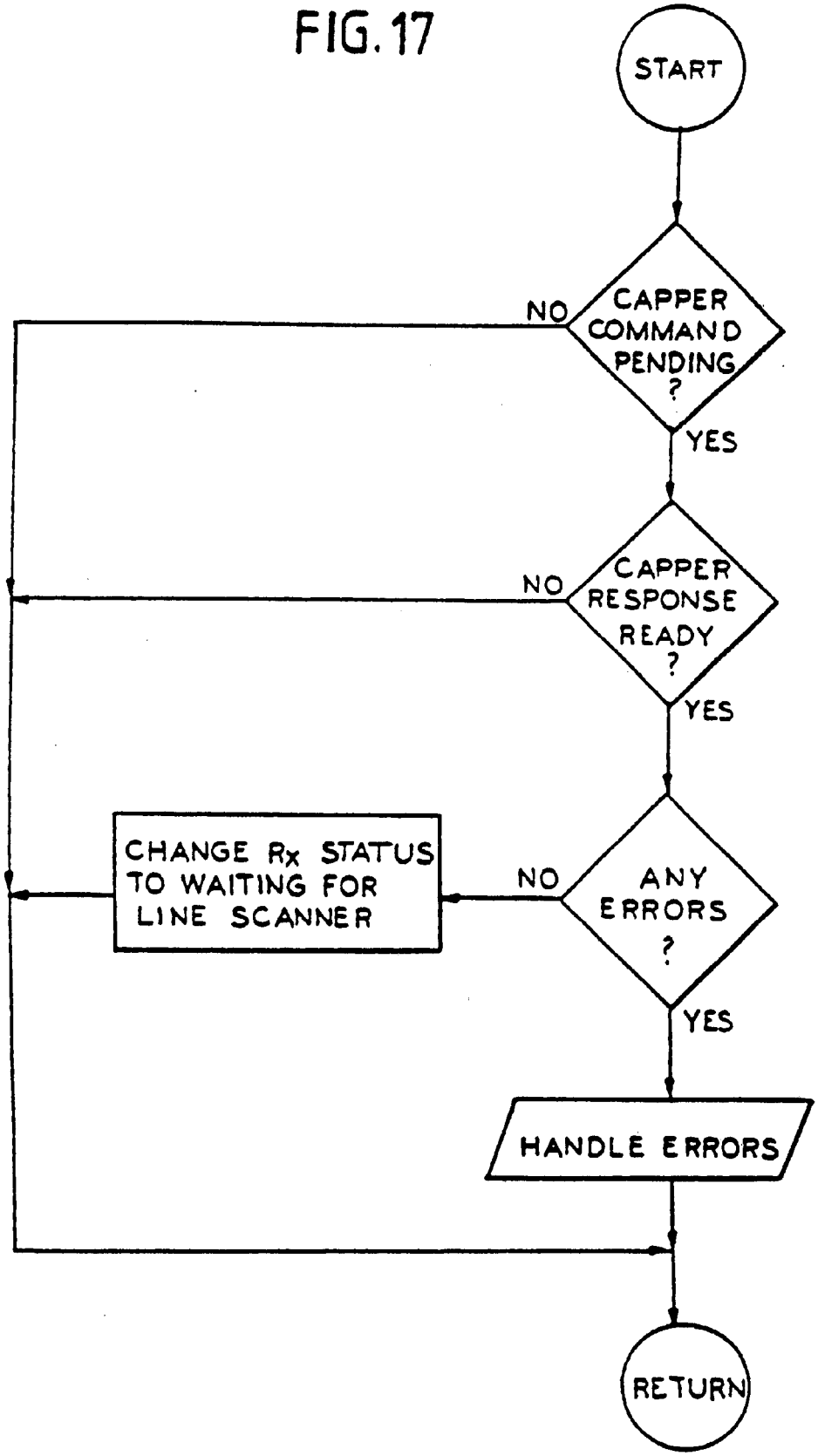
FIG. 17 is a flow diagram for a capper check process.

As illustrated in FIG. 17, when the capper is checked, a routine is invoked that, as a first step, determines whether a command is pending directing the associated capper to cap a vial, referred to as a capper command. If no capper command is pending, then the routine is terminated. If a capper command is pending, then a determination is made as to whether a capper response is ready. If a capper response is not ready, then the routine is terminated. If a capper response is ready, then a determination is made as to whether any errors have been detected in the filling process. If no errors have been detected, then the prescription status is assigned a status of "waiting for line scanner." If errors are detected, then the error handling routine is invoked and the capper check routine is terminated.

LINE SCANNER CHECK

Figure 18:
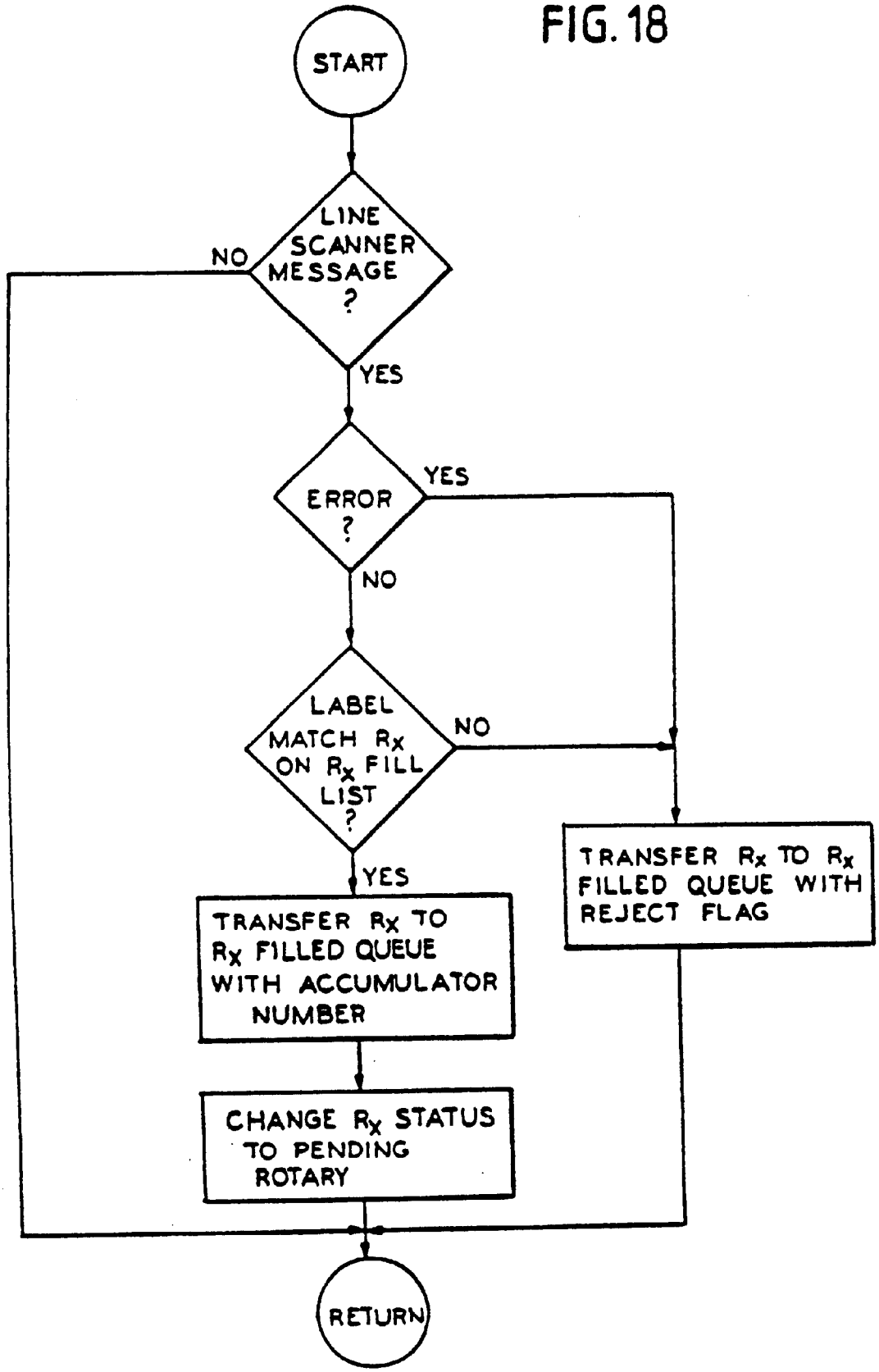
FIG. 18 is a flow diagram for a line scanner check process.

As illustrated in FIG. 18, when the line scanner is checked, a routine is invoked that determines whether a line scanner message is present. If no line scanner message is present, then the routine is terminated. If a line scanner message is present, then a determination is made as to whether an error is detected. If no error is detected, then a determination is made as to whether there is a match between the prescription information on the label and the appropriate prescription information in the Prescription Fill List 114. If the label and the Prescription Fill List information match, then the prescription is transferred to the Prescription Filled Queue 118 with an accumulator area number. Subsequently, the prescription is assigned a status of "pending rotary" and the line scanner routine check is terminated. If an error is detected or if there is no match between the label and the Prescription Fill List information the prescription is transferred to a Prescription Filled Queue 118 with a reject flag. Then the check line scanner routine is terminated.

ACCUMULATOR CHECK

Figures 19, 20:
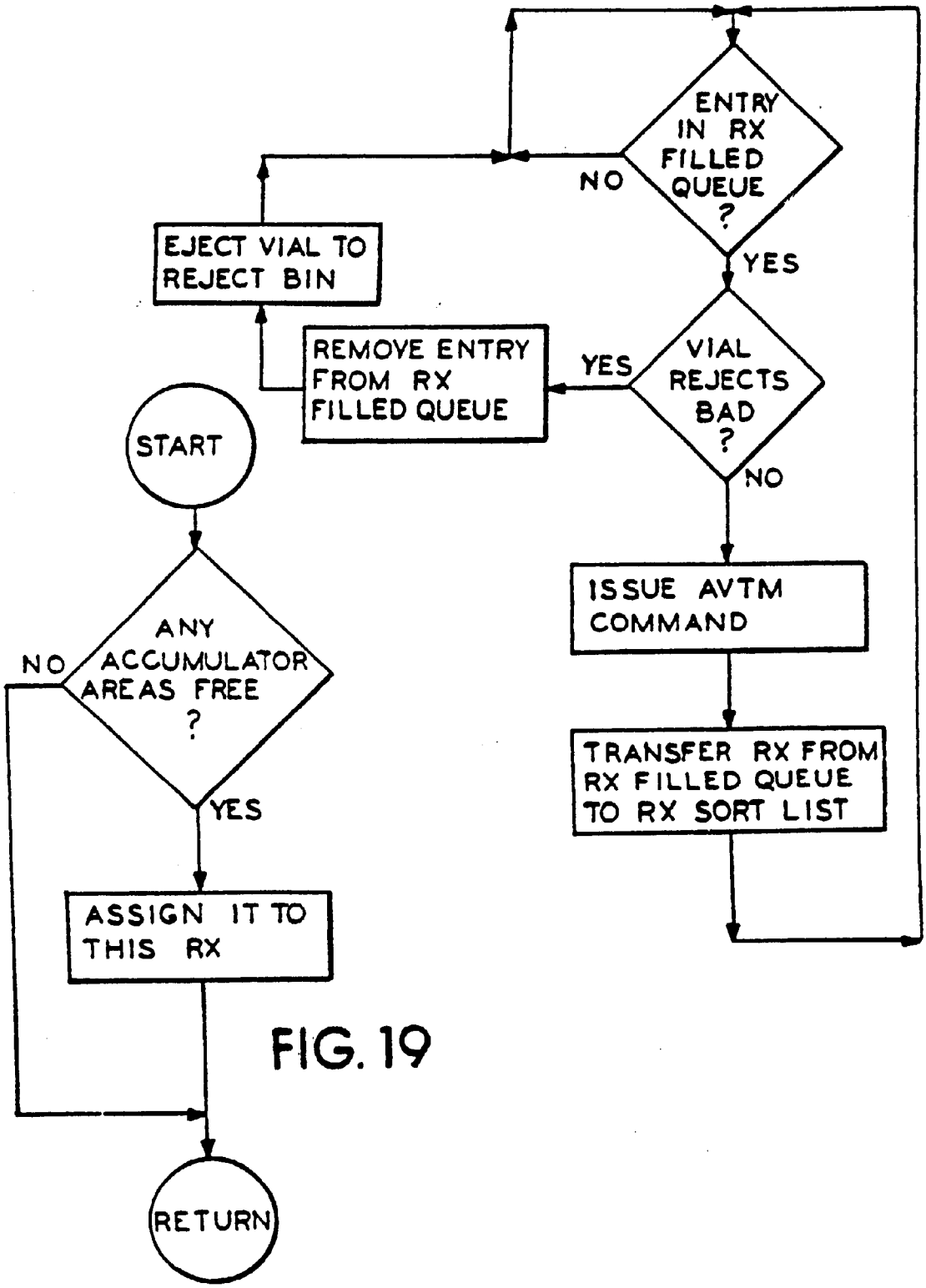
FIG. 19 is a flow diagram for an accumulator check process.
FIG. 20 is a flow diagram for a staging input process.

As illustrated in FIG. 19, when the associated accumulator 32 is checked to determine whether a free area exists. If an accumulator area is free, it is assigned. If no areas are free, then a routine is terminated.

STAGING INPUT PROCESS

As illustrated in FIG. 20, the Staging Input Process 210 removes prescriptions from the Prescription Filled Queue 118 in a FIFO order. This process also determines if the prescription flagged is "good," i.e., not rejected. If the prescription is flagged as good, then it is deposited onto the accumulator staging conveyor 37 by conveyor and placed into its assigned accumulator area by an accumulator vial transport mechanism (AVTM). The prescription is then removed from the Prescription Filled Queue 118 and placed at the tail end of the Prescription Sort List 110.

If the prescription is flagged as bad, a command removes the prescription order from the Prescription filled queue. The vial is ejected into the reject bin by a blast of air prior to reaching the accumulator staging area and its assigned accumulator area is freed up.

To accomplish the foregoing, as a first step, this process determines whether there is an entry in the Prescription Filled Queue 118. If no entry is made, then this routine loops until an entry is made in the Prescription Filled Queue 118. Subsequently, the prescription information is transferred from the Prescription Filled Queue 118 to the Prescription Sort List 110 and the staging input process routine recommences.

PRESCRIPTION SORT PROCESS

Figure 21:
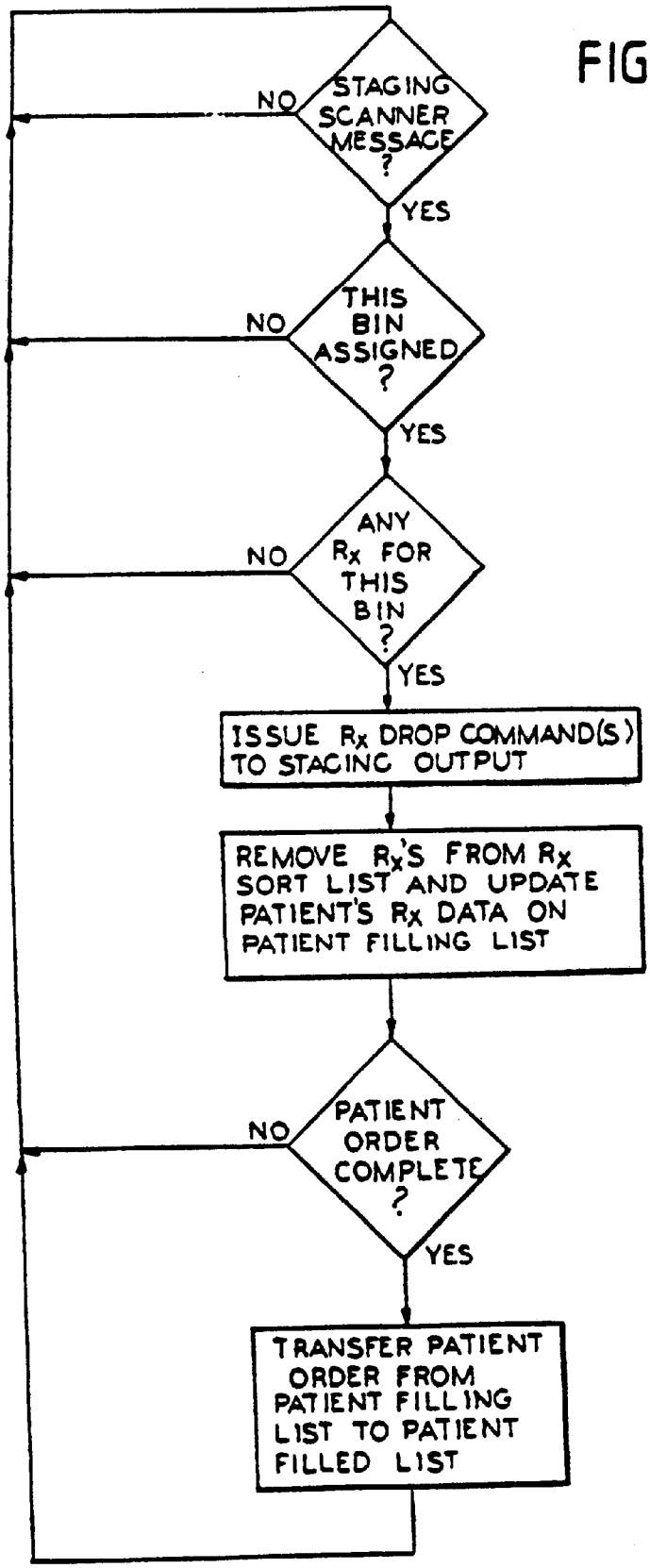
FIG. 21 is a flow diagram for a prescription sort process.

As illustrated in FIG. 21, in the Prescription Sort Process 212, prescriptions in a staging area are matched with the bins 40 as they approach those staging areas. As a bin approaches a staging area it is checked for assignment to a patient. If it is assigned to a patient, the patient's information is found in the Patient Filling List 106. This list entry is then used to check if any of the prescriptions in the Prescription Sort Lists 110 (i.e., those vials in the accumulator areas) need to be dropped into this bin. If a prescription needs to be dropped into this bin, it is removed from the Prescription Sort List 110 and placed at the tail end of the associated Prescription Sorted List 120. The patient order is then checked for completion (i.e., all prescriptions dropped into the patient's bin). If the patient's order is complete, the patient's order is removed from the Patient Filling List 106 and placed at the tail end of the Patient Filling List.

In a routine for this process, as a first step, a determination is made as to whether a staging scanner message exists. If no message exists, then the routine loops back to the beginning. If staging scanner message exists, then a determination is made as to whether a bin is assigned. If a bin is not assigned, then the routine recommences. If a bin is assigned to a patient, then a determination is made as to whether any prescriptions are to be placed in the assigned bin. If no prescriptions are to be placed in this bin, then the prescription routine recommences. If prescriptions are to be placed in the bin, then a command is issued to drop the vials to the staging output. Subsequently, the prescription is removed from the Prescription Sort List 110 and the patient's prescription status is updated on the Patient Filling List 106. Then, a determination is made as to whether a patient's order is complete. If a patient's order is not complete, the routine is recommended. If the patient's order is complete, then the patient's order is transferred from the Patient Filling List 122 to a patient filled list.

STAGING OUTPUT PROCESS

Figure 22:
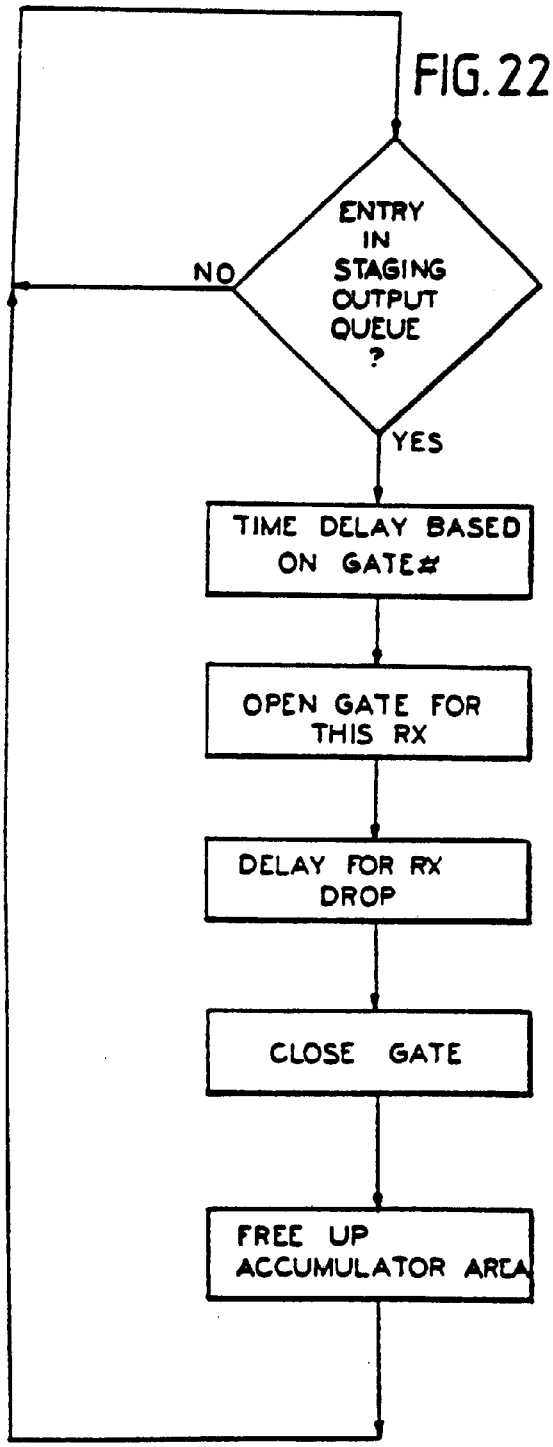
FIG. 22 is a flow diagram for a staging output process.

In the Staging Output Process 214, output gates are opened and closed at the appropriate times to drop a vial containing a prescription into a bin as it passes by on the sorting conveyor. A routine for this process, illustrated in FIG. 22, commences with a determination as to whether an entry is present in the Prescription Sorted List 120. If no entry is present, then the routine loops until an entry is present in the Prescription Sorted List 120. Once an entry is present in the Prescription Sorted List 120, a time delay is induced based on the gate number assigned to the prescription. Then, the appropriate gate is opened for the vial and held open for a predetermined delay. Subsequently, the gate is closed and the associated accumulator area is allowed to free up. Then, the staging output process recommences.

MAIL ORDER/PICK-UP DELIVERY PROCESS

Every time a bin passes by the mail order/pick-up scanners, a Mail Order/Pick-Up Delivery Process 216 checks to see if the bin is assigned to a patient. If it is, this process checks to see if this patient order is filled by checking the Patient Filled List 122. If a match occurs, this process signals a mail order/pick-up extraction process to push the bin onto the appropriate conveyor and the patient order is removed from the Patient Filled List 122.

Figure 23:
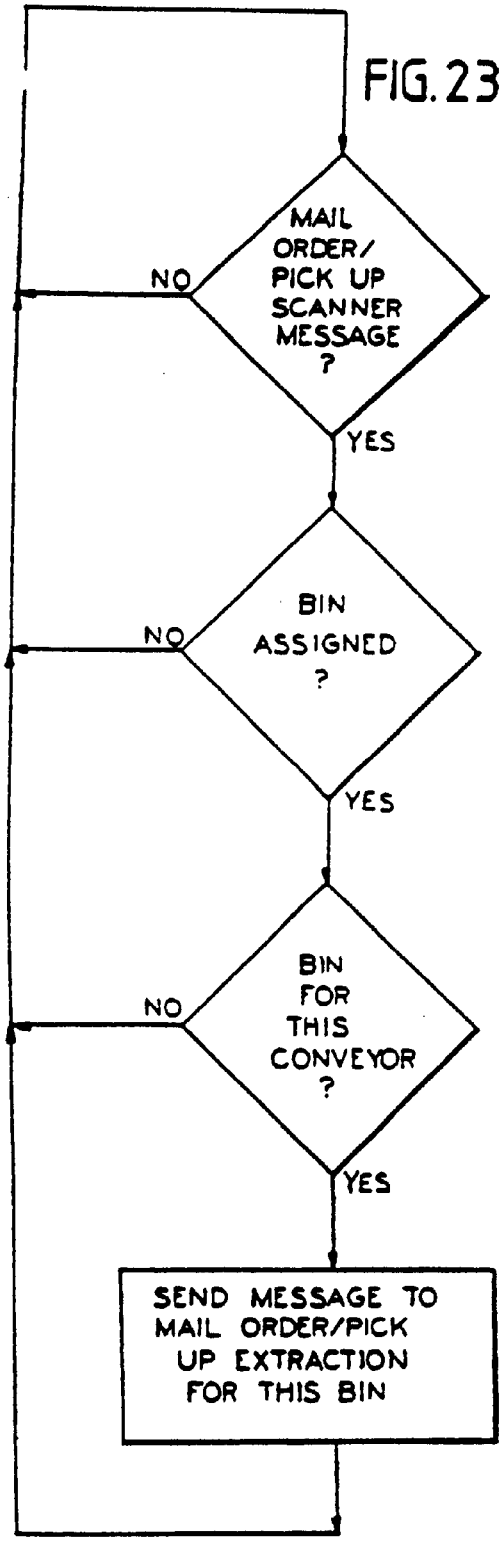
FIG. 23 is a flow diagram for a mail order/pick-up delivery process.

In a routine for this process, illustrated in FIG. 23, as a first step, a determination is made as to whether a mail order/pick-up scanner identifies a message indicating that a patient order is completed. If no such message exists on the bin, then the routine loops until such a bin passes by the scanner. If a bin includes a completed patient order, a determination is made as to whether the bin is assigned. If the bin is not assigned, then the routine recommences. If the bin is assigned, then a determination is made as to whether the bin is for a particular conveyor such as the mail order conveyor 52. If the bin is not for that conveyor, then the routine is recommenced. If the bin is for that conveyor, then a message is generated to the extraction process assigned to the conveyor. Subsequently, the routine is recommenced.

MAIL ORDER/PICK-UP EXTRACTION PROCESS

The mail order/pick-up extraction process 218 is a routine used to direct bins to one of the conveyors 52 or 54. This process, upon receiving a signal to extract a bin, starts a time delay to allow the bin to travel from the associated mail order or pick-up scanner to the extractor before issuing a command to extend the associated extractor.

Figure 24:
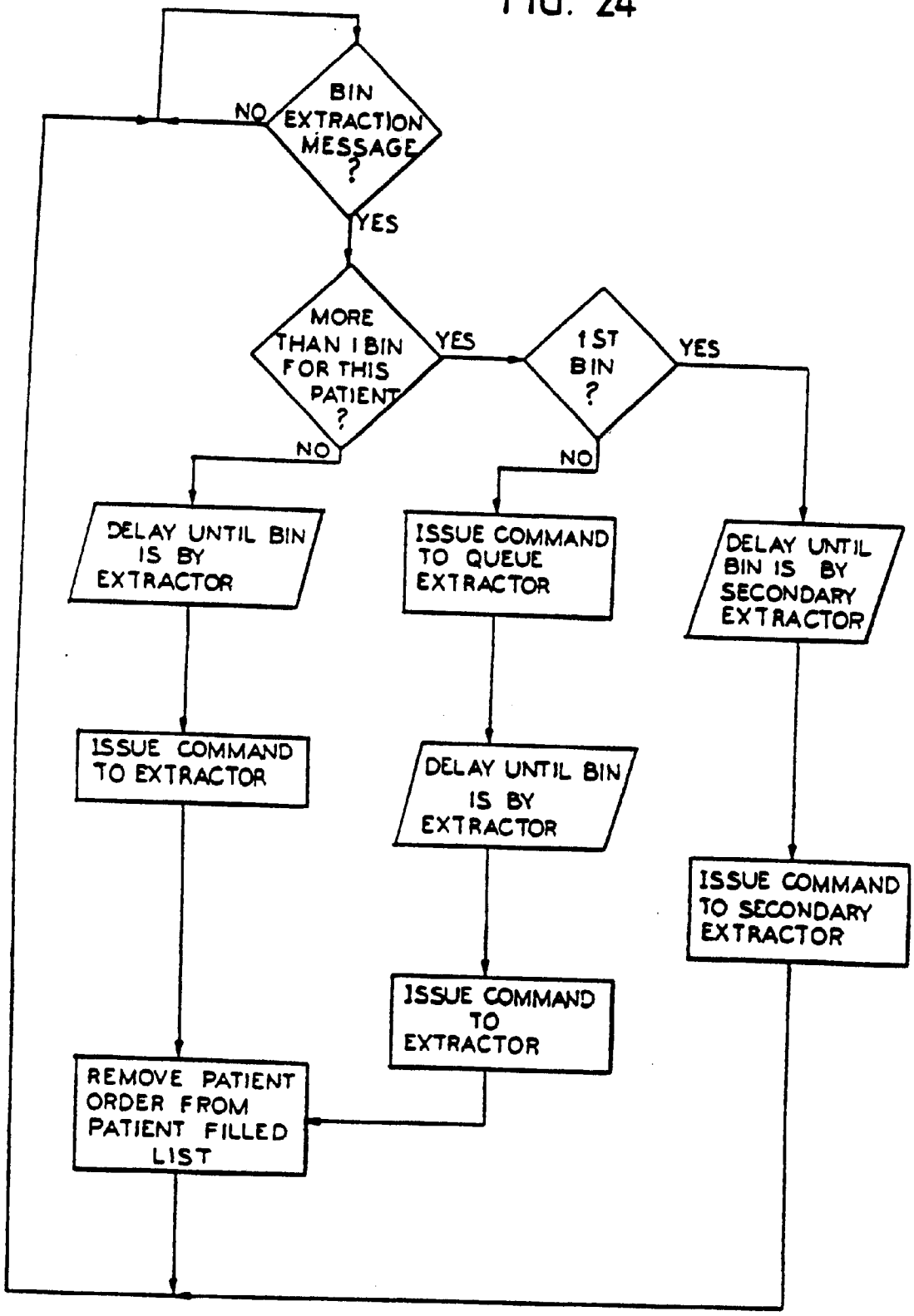
FIG. 24 is a flow diagram for a mail order/pick-up extraction process.

In a routine for this process, illustrated in FIG. 24, a first determination is made as to whether a bin extraction signal has been issued from a scanner. If no such message exists, then the routine loops until such a message is issued. If such a message exists, then a determination is made as to whether more than one bin has been assigned to this patient. If more than one bin has not been assigned to a particular patient, then a delay is inserted until the bin is adjacent the extractor. At that point, a command is issued to the extractor to place the bin on the appropriate conveyor, i.e., either the exception conveyor 50, the mail order conveyor 52, or the pick-up conveyor 54. Then the patient order is removed from the Patient Filled List 122 and the routine recommences.

If more than one bin is assigned to a particular patient, determination is made as to whether it is the first bin. If it is the first bin, a delay is induced until the bin is by a secondary extractor. At that point, a command is issued to the secondary extractor to place the first bin on the appropriate conveyor.

If the bin encounters one of several and is not the first bin assigned to the patient, then a command is issued to the extractor Queue. Then a delay is induced until the bin is by the extractor. At that point, a command is issued to the extractor to place the bin on the assigned conveyor. Then, the patient order is removed from the Patient Filled List 122 and the routine is recommenced.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A system for automatically filling prescriptions comprising:

means for receiving a patient's order, said order comprising patient identification information and one or more prescriptions;

[at least one prescription filling line including machines for automatically filling, labeling, and capping vials with drugs;]

means for assigning one of said prescriptions to [said] *at least one* prescription filling line for processing;

*the at least one prescription filling line serving to automatically process the assigned prescription without human intervention and comprising:*

*vial filling means for filling at least one discrete vial with oral solid medication according to the prescription, said vial defining a re-closable vial opening and said medication being selected from a plurality of different bulk-form oral solid medications;*

*labeling means for placing a label including information on the vial;*

*capping means for closing the vial opening with a replaceable cap after filling; and*

*vial-transport means for automatically moving the vial about the filling, labeling and capping means and to a means for vial-receiving and sorting;*

*the receiving and sorting* means [for] receiving vials from said *prescription* filling line and [for] *automatically* sorting said vials according to patient orders; and means for *automatically* collecting vials pertaining to one patient's order.

2. The system of claim 1, wherein said means for receiving vials from said filling line and for sorting said vials comprises an accumulator positioned at a terminus of said filling line operative to position a vial received from said filling line in a designated accumulator area.

3. The system of claim 1, wherein said means for collecting vials comprises a conveyor disposed adjacent the terminus of said filling line and selectable receptacles carried by said conveyor, said selectable receptacles operative to receive therein vials.

4. The system of claim 3 further comprising means for removing said receptacles from said conveyor and for directing said receptacles to one of a plurality of spurs.

5. A system for automatically filling prescriptions, comprising:

a controller for receiving a patient order, said order comprising patient identification information and at least one prescription;

*automated prescription filling apparatus operatively controlled by the controller for automatically processing the order without human intervention comprising:* at least one filling line conveyor;

a device for storing at least one empty vial associated with said filling line conveyor*, each vial defining a re-closable vial opening*;

an unscrambler disposed along said filling line conveyor for retrieving said vial and to position said vial on said filling line conveyor;

a filler positioned along said filling line conveyor downstream of said unscrambler [for placing drugs in said vial in accordance with said prescription] *and including plural canisters each for storing a discrete type of oral solid medication in bulk, the filler directing selected medication into the vial in accordance with said order*;

a labeler positioned along said filling *line* conveyor downstream of said filler for applying a label to said vial;

a capper positioned along said filling line conveyor downstream of said filler for securing a *replaceable* cap [on] *over the opening of* said vial;

an accumulator positioned at a downstream end of said filling line conveyor for receiving said vial;

a sorting conveyor disposed adjacent said accumulator;

at least one removable receptacle carried on said sorting conveyor; and a device for transferring said vial from said accumulator to said receptacle.

6. The system of claim 5, wherein said receptacle is coded, and said system includes a reader disposed adjacent said sorting conveyor so that said reader can read a code on said receptacle, said reader being in communication with said controller so that said receptacle can be correlated with a particular order.

7. The system of claim 5, further including at least one spur adjacent said sorting conveyor and a device for transferring said receptacle from said sorting conveyor to said spur.

8. The system of claim 7, comprising a plurality of spurs disposed adjacent said sorting conveyor and said device for transferring said receptacle to a spur selectively transfers said receptacle to any of said spurs.

9. The system of claim 6, including a plurality of filling line conveyors, each filling line conveyor having associated therewith a device storing at least one vial, an unscrambler, a filler, a labeler, a capper and an accumulator; said sorting conveyor running adjacent said accumulator.

10. The system of claim 9, wherein said device storing at least one vial stores a vial of a different volume.

11. A method for filling a prescription comprising the steps of:

waiting for presentation of a patient order, said order comprising one or more prescriptions and patient identification information;

determining whether said order is valid;

rejecting an invalid order;

placing said order in a first-in, first-out list if said order is valid;

acknowledging placement of said order on said first-in, first-out list;

assigning each prescription in said order to a separate filling process;

assigning a collection receptacle to said order, receiving said filled prescriptions from said filling process;

determining a vial size required to fill a prescription;

determining whether filling the prescription will deplete a drug supply below a minimum;

determining whether filling the prescription will fully deplete the drug supply; and terminating the process if filling the prescription will fully deplete the drug supply.

12. A method for filling prescriptions comprising the steps of:

providing a patient order, said order comprising patient identification data and at least one prescription;

assigning each prescription in said order to a separate filling process;

assigning a collection receptacle to said order, said receptacle receiving filled prescriptions from said filling process;

determining a vial size required to fill a prescription;

determining whether filling the prescription will deplete a drug supply below a minimum;

generating a re-fill request [is] *if* filling the prescription will deplete the drug supply below the minimum;

determining whether the prescription will fully deplete the requisite drug supply; and terminating the process if filling the prescription will fully deplete the drug supply.

13. A system for *automatically* filling prescriptions, comprising:

at least one *automated* filling line including devices for automatically filling a vial with prescribed drugs, [labelling] *labeling* said vial, and capping said vial[;] *without human intervention comprising:*

*a vial-transport mechanism positioned to transport the vial to filler apparatus and receive the filled, capped vial from a capper;*

*the filler apparatus is positioned to receive the vial from the vial-transport mechanism and includes plural canisters each for storing a discrete type of oral solid medication in bulk, the filler apparatus directing the prescribed drugs into the vial from at least one canister;*

*labeler apparatus positioned to receive the vial, the labeler including labeling apparatus for applying a label with information to the vial;*

*the capper is positioned to receive the filled vial, the capper including capping apparatus for applying a replaceable cap on the vial;* a sorting system disposed at a terminal of said filling line for receiving [vials therefrom] *said vial from the vial-transport mechanism* and *automatically* transporting collections of said vials, each collection pertaining to a particular patient; and a control system for controlling said filling line [in] *and* said sorting system.

14. The prescription filling system of claim 13, wherein said sorting system includes a plurality of receptacles, each receptacle being coded with information so that said receptacles can be temporarily correlated with a particular patient.

15. The prescription filling system of claim 13, wherein said control system includes a plurality of lists to which prescription information is successively transferred during processing of a prescription.

*16. The method of claim 11 including the further step of, if the requisite drug supply is available, automatically filling the prescription.*

*17. The method of claim 12 including the further step of, if the requisite drug supply is available, automatically filling the prescription.*

*18. A system for automatically filling patient prescription orders, the system comprising:*

*a control system for receiving a patient's prescription order, said order including patient identification and prescription information, and for controlling apparatus for automatically filling at least one prescription corresponding to the patient's prescription order;*

*at least one prescription filling line operatively controlled by the control system including machine structure for automatically filling and labeling at least one discrete vial without human intervention in accordance with the patient's prescription order, said at least one vial having a surface and defining a re-closable vial opening and the filling line machine structure including:*

*a vial-transport mechanism configured to automatically transport the at least one vial between at least a first position in which the empty vial is received by the vial-transport mechanism, another position in which the empty vial is transported to vial-filler apparatus and a further position in which the filled vial is transported to a vial accumulator;*

*the vial-filler apparatus is positioned to receive the empty vial transported by the vial-transport mechanism and includes plural canisters each for storing a discrete type of oral solid medication in bulk, the vial-filler automatically dispensing oral solid medication from at least one of said canisters and into said vial in accordance with the prescription order; and*

*vial-labeler apparatus positioned with respect to the filling line and including labeler apparatus configured to place a label including information on the vial surface;*

*the vial accumulator being operatively controlled by the control system and positioned to receive the at least one discrete vial from the filling line vial-transport mechanism, the accumulator including vial receiving and sorting structure, said sorting structure automatically sorting the at least one vial according to the prescription order; and*

*a vial collector operatively controlled by the control system and positioned with respect to the accumulator to receive the at least one sorted vial from the accumulator pertaining to the patient's prescription order.*

*19. The system of claim 18 including two prescription filling lines.*

*20. The system of claim 19 wherein the control system assigns the prescription to the filling line capable of most efficiently filling the discrete vials with the prescribed drugs.*

*21. The system of claim 18 wherein the filling line further includes vial capper apparatus positioned to receive the filled vial and automatically apply a replaceable cap across the vial opening.*

*22. A system for automatically filling patient prescription orders, the system comprising:*

*a control system for receiving a patient's prescription order and for controlling apparatus for automatically filling at least one prescription corresponding to the patient's prescription order;*

*at least one filling line operatively controlled by the control system including machine structure for automatically filling and labeling at least one discrete vial according to the patient's prescription order without human intervention, the vial defining a re-closable vial opening and having at least one vial surface, and the filling line machine structure including:*

*a vial-transport mechanism configured to automatically transport the at least one vial between at least a first position in which the empty vial is received by the vial-transport mechanism, another position in which the empty vial is transported to vial-filler apparatus and a further position in which the filled vial is transported to a filling line terminal end;*

*the vial-filler apparatus is positioned to receive the empty vial transported by the vial-transport mechanism and includes plural canisters each for storing a discrete type of oral solid medication in bulk, the vial-filler automatically dispensing oral solid medication from at least one of said canisters and into said vial in accordance with the prescription order; and*

*vial-labeler apparatus positioned with respect to the filling line and including labeler apparatus configured to place a label including information on the vial surface;*

*a system disposed at the terminal end of the filling line operatively controlled by the control system including machine structure configured to receive the at least one discrete, filled vial from the vial-transport mechanism and automatically collect said at least one vial corresponding to the patient's order.*

*23. The system of claim 22 including two prescription filling lines.*

*24. The system of claim 22 wherein the filling line further includes vial capping apparatus positioned to receive the at least one filled vial and automatically apply a replaceable cap over the vial opening.*

*25. A method for automatically filling patient prescription orders without human intervention comprising the steps of:*

*providing a patient's prescription order, said order comprising patient identification and prescription data, to a control system for controlling a vial filling line and apparatus for collecting vials corresponding to the patient's prescription order;*

*providing at least one filling line operatively controlled by the control system including machines for automatically transporting, filling and labeling discrete vials corresponding to the patient's prescription order, each of said vials having at least one surface defining a vial opening;*

*providing at least one machine, operatively controlled by the control system, for automatically collecting the filled, labeled discrete vials corresponding to the patient's order;*

*automatically transporting at least one empty vial to the filling machine based on at least one command from the control system;*

*automatically filling the at least one discrete vial with the filling machine, said filling machine automatically placing bulk-form medication in said at least one vial corresponding to the patient's prescription order based on at least one command from the control system;*

*during or after the filling step, automatically placing a label on the surface of said at least one vial based on at least one command from the control system;*

*automatically transporting said filled, labeled at least one vial to the collecting machine based on at least one command from the control system; and*

*automatically collecting filled, labeled vials corresponding to the patient's prescription order based on at least one command from the control system.*

*26. The method of claim 25 further comprising the step of before the filling step, receiving a plurality of unfilled vials for selective transport to the filling line.*

*27. The method of claim 26 further comprising the step of before the filling step, transporting a collection of the plurality of unfilled vials to the filling line wherein the collection pertains to a particular patient.*

*28. The method of claim 25 further comprising the step of providing at least two filling lines.*

*29. The method of claim 28 further comprising the step of before the filling step, assigning each prescription in said order to the filling line capable of most efficiently filling the patient's order.*

*30. The method of claim 25 further comprising the steps of:*

*providing at least one machine, operatively controlled by the control system, for automatically capping the at least one filled, labeled discrete vial corresponding to the patient's prescription order; and*

*after the filling step, automatically capping the re-closable vials with a reusable cap placed over the vial opening based on at least one command from the control system.*

*31. A method for automatically filing patient prescription orders with medication in at least one discrete vial defining a re-closable vial opening and having a vial surface, said medication corresponding to a person's prescription order and for automatically collecting the at least one filled, labeled vial corresponding to the person's prescription order comprising the steps of:*

*providing a person's prescription order to a control system for processing said prescription order and for controlling a filling line comprising automated apparatus for transporting, filling and labeling discrete vials and for controlling apparatus for collecting the filled, labeled vials corresponding to the prescription order;*

*providing the filling line comprising automated apparatus for transporting, filling and labeling discrete vials and apparatus for collecting the filled, labeled vials corresponding to the prescription order;*

*providing at least one command from the control system to the automated vial transporting apparatus whereby at least one empty vial is transported to the filling and labeling apparatus;*

*providing at least one command from the control system to the automated apparatus for filling and labeling whereby the at least one discrete vial is, in no particular order, automatically filled with medication corresponding to the patient's prescription order and automatically labeled with patient prescription information;*

*providing at least one command from the control system to the automated vial transporting apparatus whereby the at least one filled, labeled vial is transported to the automated vial-collecting apparatus; and*

*providing at least one command from the control system to the automated vial-collecting apparatus whereby the at least one filled, labeled vial is collected corresponding to the patient's prescription order.*

*32. The method of claim 31 wherein apparatus for automatically capping a filled, labeled discrete vial is provided and further including the step of providing at least one command from the control system to the automated capping apparatus whereby the at least one filled vial is capped with a reusable cap placed over the vial opening.*

*33. The method of claim 31 further including the step of providing at least two filling lines controlled by the control system.*

*34. The method of claim 33 further including the step of, before the filling step, assigning each prescription in said patient prescription order to the filling line capable of most efficiently filling the patient prescription order.*

* * * * *

UNITED STATES PATENT AND TRADEMARK OFFICE

CERTIFICATE OF CORRECTION

PATENT NO. : RE 37,829 E
DATED : September 3, 2002
INVENTOR(S) : Charhut et al.

It is certified that error appears in the above-identified patent and that said Letters Patent is hereby corrected as shown below:

Title page,
Item [75], Inventors, after "Charhut," delete "Tokyo (JP)" and substitute therefor -- Mission Viejo, CA (US) --; after "Goodale," delete "Park City" and substitute therefor -- Gurnee --; after "Blechl," delete "Ingleside, IL" and substitute therefor -- Saint Peters, MO --; and after "Skou," delete "Des Plaines" and substitute therefor -- Arlington Heights --.

Column 15,
Line 32, after "order," insert -- said receptacle --;
Line 33, before "filled," delete "said";
Lines 37-40, "determining whether filling the prescription will fully deplete the drug supply; and terminating the process if filling the prescription will fully deplete the drug supply."
should be
-- determining whether filling the prescription will fully deplete the drug supply; and terminating the process if filling the prescription will fully deplete the drug supply. --.

Column 18,
Line 54, delete "filing" and substitute therefor -- filling --;
Lines 57, 59 and 61, delete "person's" and substitute therefor -- patient's --.

Signed and Sealed this

Twenty-fifth Day of November, 2003

JAMES E. ROGAN
*Director of the United States Patent and Trademark Office*